(12) United States Patent
Wakamiya

(10) Patent No.: US 9,201,083 B2
(45) Date of Patent: Dec. 1, 2015

(54) SAMPLE ANALYZER AND REAGENT MANAGEMENT METHOD

(75) Inventor: Yuji Wakamiya, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 1240 days.

(21) Appl. No.: 13/045,077

(22) Filed: Mar. 10, 2011

(65) Prior Publication Data

US 2011/0223682 A1 Sep. 15, 2011

(30) Foreign Application Priority Data

Mar. 11, 2010 (JP) .................................. 2010-054901
Mar. 25, 2010 (JP) .................................. 2010-070663

(51) Int. Cl.
*G01N 1/10* (2006.01)
*G01N 33/00* (2006.01)
*G01N 35/00* (2006.01)

(52) U.S. Cl.
CPC ..................... *G01N 35/00732* (2013.01); *G01N 2035/00851* (2013.01); *Y10T 436/2575* (2015.01)

(58) Field of Classification Search
CPC .......... G01N 2035/00851; G01N 2035/00782; G01N 2035/00811; G01N 2035/00831; G01N 2035/00742; G01N 35/00732; Y10T 436/2575
See application file for complete search history.

(56) References Cited

U.S. PATENT DOCUMENTS

| | | | |
|---|---|---|---|
| 2006/0199196 A1* | 9/2006 | O'Banion et al. | ................. 435/6 |
| 2007/0255756 A1 | 11/2007 | Satomura | |
| 2008/0240991 A1 | 10/2008 | Wakamiya et al. | |
| 2008/0241937 A1* | 10/2008 | Wakamiya et al. | .............. 436/43 |
| 2010/0001876 A1* | 1/2010 | Sasaki | ....................... 340/825.22 |

FOREIGN PATENT DOCUMENTS

| | | |
|---|---|---|
| CN | 101275961 A | 10/2008 |
| EP | 0637750 A2 | 2/1995 |
| JP | 08-094626 | 4/1996 |
| JP | 09-127136 A | 5/1997 |
| JP | 2008203007 A | 9/2008 |
| WO | 2009142087 A1 | 11/2009 |

* cited by examiner

*Primary Examiner* — Christopher A Hixson
(74) *Attorney, Agent, or Firm* — Sughrue Mion, PLLC

(57) ABSTRACT

A sample analyzer for performing analysis regarding a predetermined measurement item by using a combination of at least a first reagent and a second reagent, the sample analyzer comprising: a reagent container holder configured to hold a first reagent container which contains the first reagent and which includes a first storage medium, and a second reagent container which contains the second reagent and which includes a second storage medium; a writer configured to write information into the first storage medium and the second storage medium; and a controller configured to control the writer to write, into the first storage medium of the first reagent container, identification information for identifying the second reagent container which is paired with the first reagent container is disclosed. A reagent management method is also disclosed.

11 Claims, 20 Drawing Sheets

FIG. 5
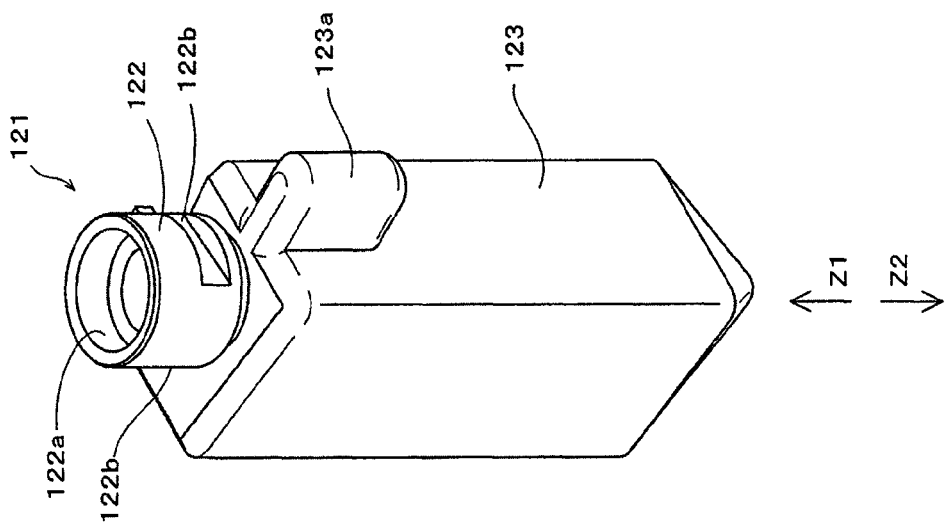
(c) R3 REAGENT CONTAINER
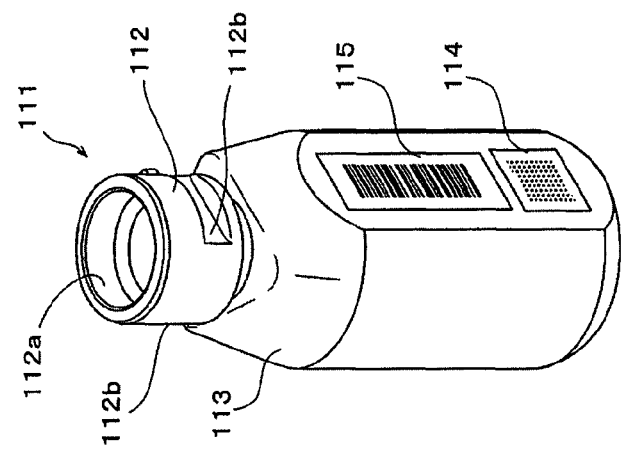
(b) R2 REAGENT CONTAINER
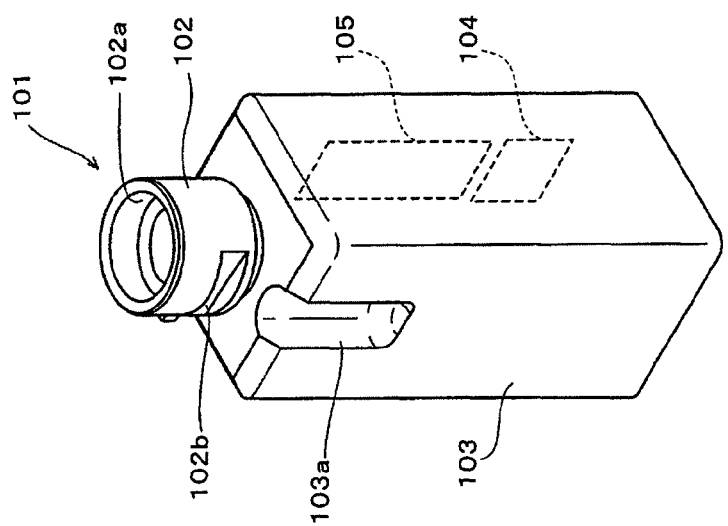
(a) R1 REAGENT CONTAINER

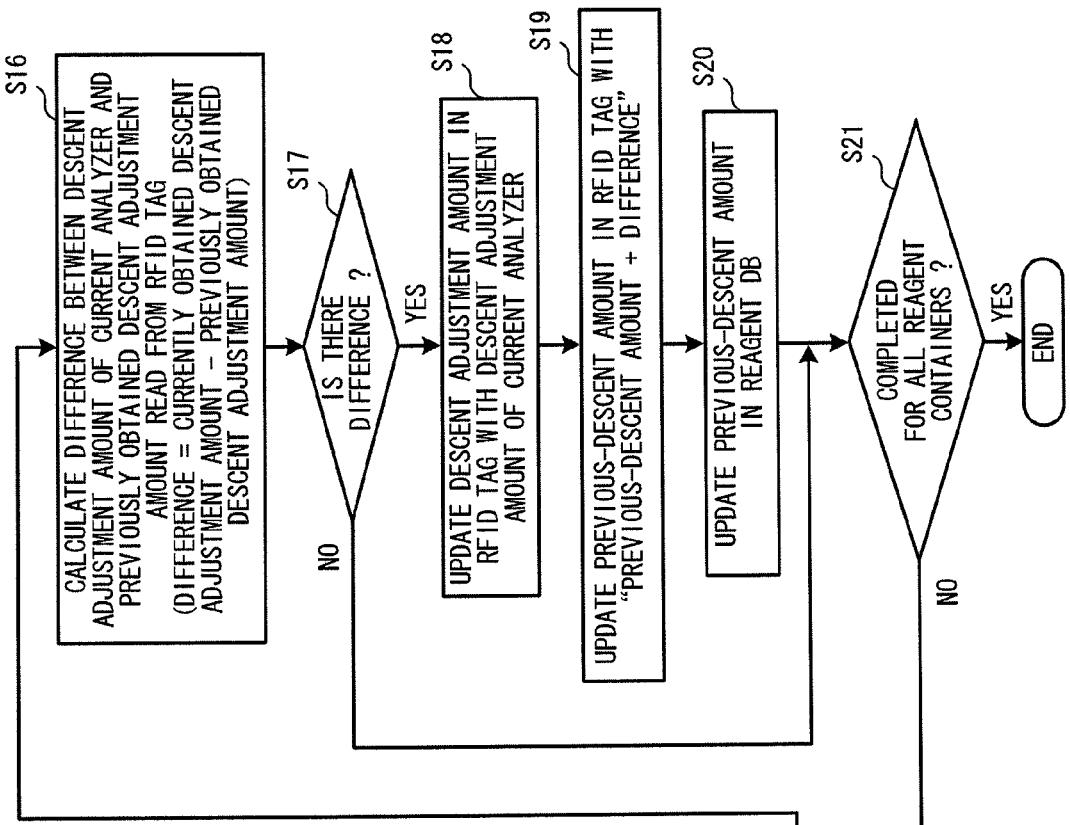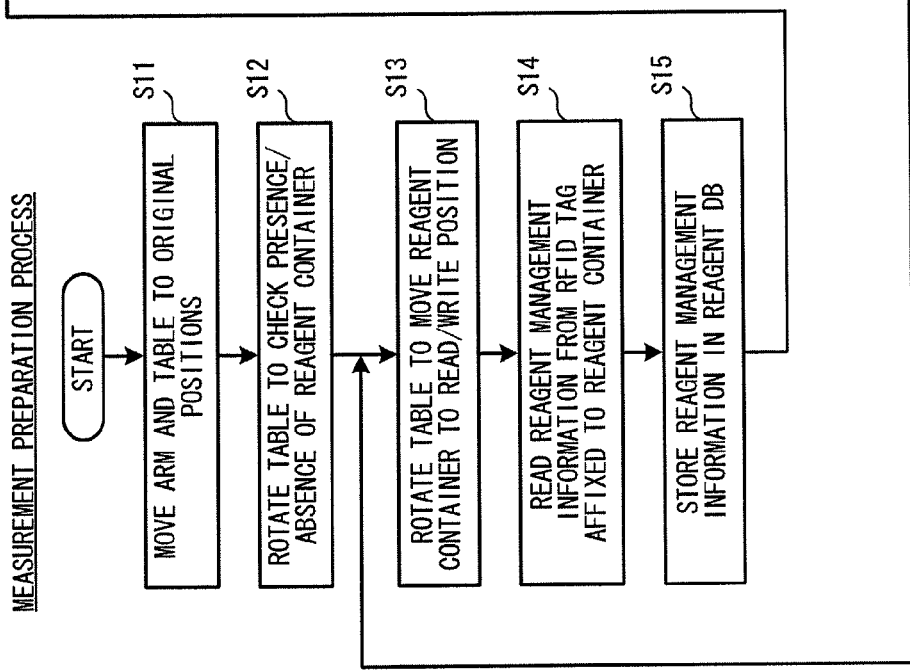
FIG. 13

(a) MEASUREMENT PROCESS (b) REAGENT ASPIRATING PROCESS

SAMPLE ANALYZER AND REAGENT MANAGEMENT METHOD

CROSS REFERENCE TO RELATED APPLICATIONS

This application claims priority from Japanese Patent Application No. 2010-054901, filed on Mar. 11, 2010, in the Japanese Patent Office and from Japanese Patent Application No. 2010-070663, filed on Mar. 25, 2010, in the Japanese Patent Office.

FIELD OF THE INVENTION

The present invention relates to a sample analyzer for performing analysis regarding a predetermined measurement item by using a combination of at least a first reagent and a second reagent, a reagent management method, and a sample analyzer that includes a reagent dispenser having a liquid surface detector.

BACKGROUND

There are known conventional sample analyzers for performing analysis regarding a predetermined measurement item by using a combination of a first reagent and a second reagent. For example, in a sample analyzer disclosed by U.S. Patent Application Publication No. 2008/0240991, a bar code reader reads reagent information from a bar code affixed to a first reagent container containing a first reagent and a bar code affixed to a second reagent container containing a second reagent. Based on the reagent information read by the bar code reader, a combination (i.e., a pair) of the first reagent container and the second reagent container is registered in a reagent DB stored in a hard disk of a control apparatus.

There is a case where the first reagent container and the second reagent container are removed from the sample analyzer and then set in a different sample analyzer. In this case, since pair information indicating the pair of the first reagent container and the second reagent container is registered only in the reagent DB of the previous sample analyzer, there is a possibility that the first reagent container and the second reagent container are not properly combined (i.e., paired) with each other in the different sample analyzer. If false pair information in which the first reagent container is erroneously paired with a different second reagent container is registered in a reagent DB of the different sample analyzer, a situation arises where the remaining amount or expiration date of the reagent in the first reagent container and the remaining amount or expiration date of the reagent in the different second reagent container do not match. In such a situation, there is a fear that a reagent that is still usable is determined to be unusable based on its remaining amount or expiration date.

There are conventional automatic analyzers that include a reagent dispending probe (hereinafter, simply referred to as a "probe") having a liquid surface detector. For example, Japanese Laid-Open Patent Publication No. H09-127136 discloses an automatic analyzer capable of storing, in a memory within the analyzer, the number of pulses that have been applied to cause the probe to descend from a reference position until the liquid surface detector detects a liquid surface (hereinafter, referred to as a "descent pulse number").

The automatic analyzer disclosed by Japanese Laid-Open Patent Publication No. H09-127136 compares the descent pulse number that is obtained when the probe detects the liquid surface with the descent pulse number that has previously been stored in the memory, and determines based on the result of the comparison whether the liquid surface detection has been properly performed. This prevents erroneous liquid surface detection caused by, for example, formation of bubbles at the liquid surface.

Assume a case where a plurality of such automatic analyzers are installed in a laboratory. In this case, if a reagent container previously used in one of the automatic analyzers is set in another one of the automatic analyzers, there is no descent pulse number previously stored for the reagent container in the memory of the other one of the automatic analyzers. Therefore, there is a fear that the other one of the automatic analyzers, in which the reagent container is set, may fail in accurately determining whether the liquid surface detection has been properly performed.

SUMMARY OF THE INVENTION

The scope of the present invention is defined solely by the appended claims, and is not affected to any degree by the statements within this summary.

A first aspect of the present invention is a sample analyzer for performing analysis regarding a predetermined measurement item by using a combination of at least a first reagent and a second reagent, the sample analyzer comprising: a reagent container holder configured to hold a first reagent container which contains the first reagent and which includes a first storage medium, and a second reagent container which contains the second reagent and which includes a second storage medium; a writer configured to write information into the first storage medium and the second storage medium; and a controller configured to control the writer to write, into the first storage medium of the first reagent container, identification information for identifying the second reagent container which is paired with the first reagent container A second aspect of the present invention is a sample analyzer for measuring a measurement sample that is prepared by mixing a sample with a reagent, the sample analyzer comprising: a reagent dispenser including an aspiration tube, which is caused to descend into a reagent container containing the reagent when aspirating the reagent, and a sensor, which is included in the aspiration tube, for detecting the liquid surface of the reagent; a writer/reader configured to write information into, and to read information from, a storage medium which is included in the reagent container; and a controller configured to control the writer/reader to write liquid surface position information into the storage medium, which liquid surface position information is obtained when the sensor detects the liquid surface of the reagent.

A third aspect of the present invention is a sample analyzer for measuring a measurement sample that is prepared by mixing a sample with a reagent, the sample analyzer comprising: a reagent dispenser including an aspiration tube, which is caused to descend into a reagent container containing the reagent when aspirating the reagent, and a sensor, which is included in the aspiration tube, for detecting the liquid surface of the reagent; and a controller, wherein the reagent container includes a storage medium configured to store liquid surface position information which is obtained when the sensor detects the liquid surface of the reagent, and the controller is configured to control the reagent dispenser based on the liquid surface position information stored in the storage medium.

A fourth aspect of the present invention is a reagent management method for combining a first reagent container containing a first reagent with a second reagent container containing a second reagent, the reagent management method comprising writing identification information into a first storage medium which is a readable/writable storage medium and which is included in the first reagent container, which identification information identifies the second reagent container which is paired with the first reagent container.

A fifth aspect of the present invention is a reagent management method executed by a sample analyzer for measuring a measurement sample that is prepared by mixing a sample with a reagent, the reagent management method comprising steps of: detecting the liquid surface of the reagent by means of a sensor included in an aspiration tube which is caused to descend into a reagent container containing the reagent when aspirating the reagent; and writing, into a storage medium included in the reagent container, liquid surface position information which is obtained when the sensor detects the liquid surface of the reagent.

BRIEF DESCRIPTION OF THE DRAWINGS

FIG. 5 is a perspective view showing structures of an R1 reagent container, an R2 reagent container, and an R3 reagent container according to the embodiment;

FIG. 13 is a flowchart showing a measurement preparation process according to the embodiment;

DETAILED DESCRIPTION OF THE EMBODIMENT (First Embodiment)

In a first embodiment of the present invention, the present invention is applied to a sample analyzer for performing tests on a sample (e.g., a blood sample) for various items such as hepatitis B, hepatitis C, tumor markers, thyroid hormones, and the like.

Figure 1:
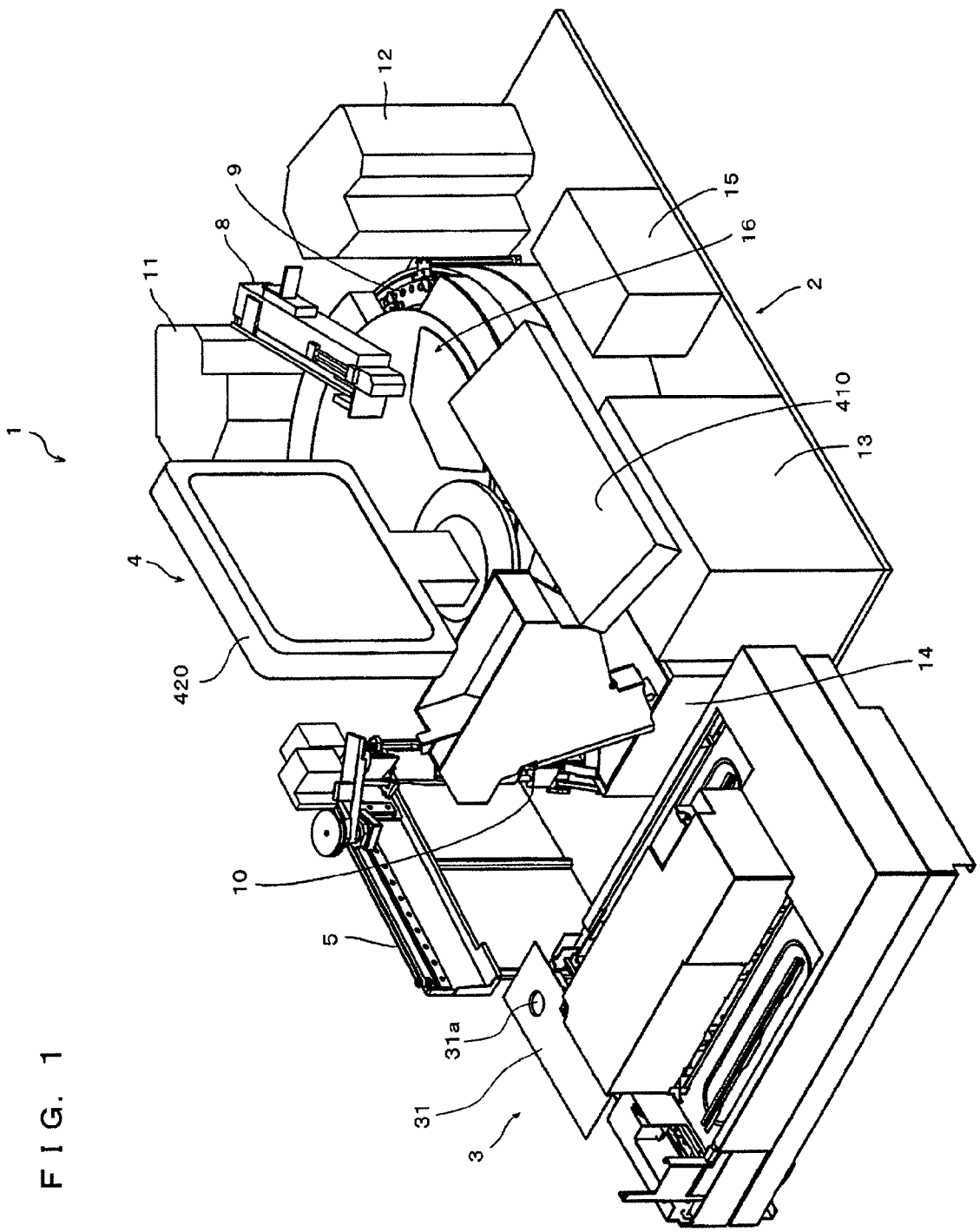
FIG. 1 is a perspective view showing an overall structure of a sample analyzer according to an embodiment of the present invention.
Figure 2:
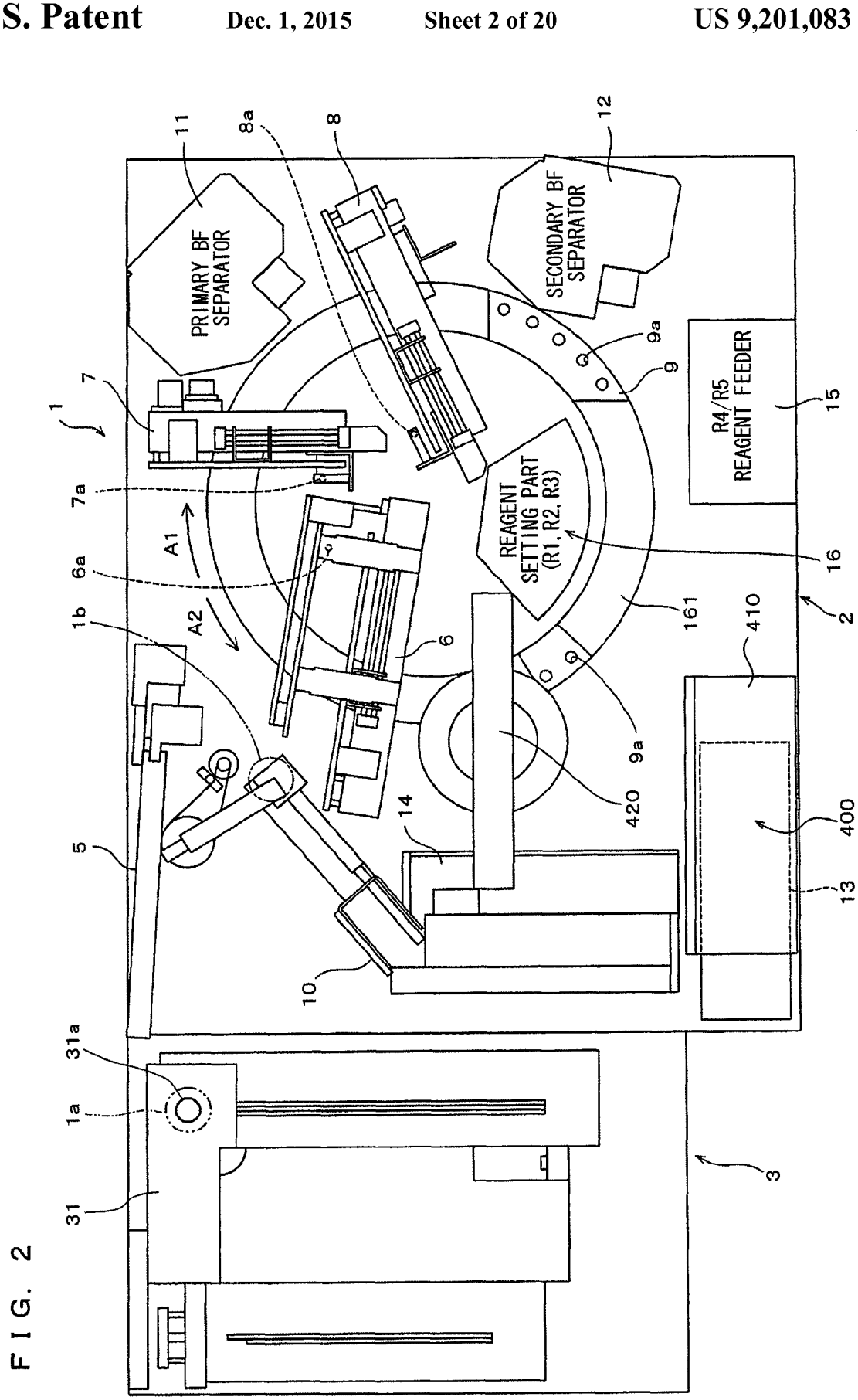
FIG. 2 is a plan view showing a structure of a measurement mechanism unit according to the embodiment, which is seen from above.

In the sample analyzer according to the present embodiment, a capture antibody (R1 reagent) bound to an antigen contained in a sample (e.g., a blood sample) to be measured is bound to magnetic particles (R2 reagent), and the antigen, the capture antibody, and the magnetic particles, which have been bound, are attracted to a magnet (not shown) of a primary BF (Bound Free) separator 11 (see FIG. 1 and FIG. 2). In this manner, the R1 reagent containing the capture antibody that is unreacted (i.e., free) is removed. Then, the antigen bound to the magnetic particles is bound to a labeled antibody (R3 reagent). Thereafter, the magnetic particles, the antigen, and the labeled antibody, which have been bound, are attracted to a magnet (not shown) of a secondary BF separator 12. In this manner, the R3 reagent containing the labeled antibody that is unreacted (i.e., free) is removed. Further, a dispersion liquid (R4 reagent) and a luminescent substrate (R5 reagent) which emits light in a reaction process with the labeled antibody are added. Thereafter, the amount of light generated by the reaction of the luminescent substrate with the labeled antibody is measured. Through this process, the antigen contained in the sample, which is bound to the labeled antibody, is quantitatively measured.

Hereinafter, the sample analyzer according to the present embodiment will be described with reference to the accompanying drawings.

FIG. 1 is a perspective view showing an overall structure of a sample analyzer 1.

The sample analyzer 1 according to the present embodiment includes a measurement mechanism unit 2, a sample transporting unit (sampler) 3 disposed adjacent to the measurement mechanism unit 2, and a control apparatus 4 electrically connected to the measurement mechanism unit 2.

The sample transporting unit 3 is configured to transport a rack that accommodates multiple test tubes containing samples. The control apparatus 4 includes a body 400 (see FIG. 9), an input unit 410, and a display unit 420. A bar code reader 17 (see FIG. 9), which is a handheld bar code reader and which has a bar code reading function, is connected to the control apparatus 4.

FIG. 2 is a plan view showing a structure of the measurement mechanism unit 2 seen from above.

The measurement mechanism unit 2 includes a sample dispensing arm 5, an R1 reagent dispensing arm 6, an R2 reagent dispensing arm 7, an R3 reagent dispensing arm 8, a reaction part 9, a cuvette feeder 10, the primary BF separator 11, the secondary BF separator 12, a pipette tip feeder 13, a detector 14, an R4/R5 reagent feeder 15, and a reagent setting part 16.

The cuvette feeder 10 is configured to accommodate multiple cuvettes and to sequentially feed cuvettes one by one to a sample discharging position 1b at which the sample dispensing arm 5 performs a sample discharging operation.

As shown in FIG. 2, a pipette 6a for aspirating and discharging the R1 reagent is attached to the R1 reagent dispensing arm 6. A stepping motor included in a reagent dispensing arm stepping motor section 211 (see FIG. 8) drives the R1 reagent dispensing arm 6 to rotate and also to move in the up/down directions (i.e., the vertical directions). The R1 reagent dispensing arm 6 aspirates, by means of the pipette 6a, the R1 reagent that is set in the reagent setting part 16, and dispenses (i.e., discharges) the aspirated R1 reagent into a cuvette that is placed at the sample discharging position 1b.

The pipette tip feeder 13 transports multiple pipette tips (not shown) that have been fed into the pipette tip feeder 13 to a tip attaching position (not shown) one by one, at which position a pipette tip is to be attached to the sample dispensing arm 5. Thereafter, at the tip attaching position, a pipette tip is attached to the end of the pipette of the sample dispensing arm 5.

After the pipette tip is attached to the pipette at the tip attaching position, the sample dispensing arm 5 aspirates, through a hole 31a formed in a top board 31 covering a transporting path of the sample transporting unit 3, a sample from a test tube that has been transported to a sample aspirating position 1a by the sample transporting unit 3, and dispenses (i.e., discharges) at the sample discharging position 1b the sample into the cuvette into which the R1 reagent dispensing arm 6 has dispensed the R1 reagent. Then, the cuvette is moved by a catcher (not shown) of the R1 reagent dispensing arm 6 to the reaction part 9.

As shown in FIG. 2, a pipette 7a for aspirating and discharging the R2 reagent is attached to the R2 reagent dispensing arm 7. A stepping motor included in the reagent dispensing arm stepping motor section 211 (see FIG. 8) drives the R2 reagent dispensing arm 7 to rotate and also to move in the up/down directions (i.e., the vertical directions). The R2 reagent dispensing arm 7 aspirates, by means of the pipette 7a, the R2 reagent that is set in the reagent setting part 16, and dispenses (i.e., discharges) the aspirated R2 reagent into the cuvette that contains the R1 reagent and the sample.

As shown in FIG. 2, the reaction part 9 is formed in an annular shape so as to surround the reagent setting part 16 which has a round shape. The reaction part 9 includes multiple cuvette setting parts 9a which are arranged along the outline of the reaction part 9 with predetermined intervals. The cuvette setting parts 9a are each formed as a round recess which allows a cuvette to be inserted (set) therein. The reaction part 9 has a function of heating cuvettes set in the cuvette setting parts 9a to approximately 42° C. In other words, in the reaction part 9, samples contained in the cuvettes are heated to approximately 42° C. This prompts reactions to occur between the samples and various reagents in the respective cuvettes. The reaction part 9 is configured to be rotatable in the clockwise direction (i.e., an arrow A1 direction), which realizes a function of moving each cuvette set in the cuvette setting parts 9a to respective positions at which various processes (e.g., reagent dispensing) are performed.

When a cuvette that contains a sample, the R1 reagent, and the R2 reagent is moved by a catcher (not shown) from the reaction part 9 to the primary BF separator 11, the primary BF separator 11 separates the R1 reagent that is unreacted (i.e., an unnecessary component) from magnetic particles in the sample contained in the cuvette (i.e., B/F separation).

As shown in FIG. 2, a pipette 8a for aspirating and discharging the R3 reagent is attached to the R3 reagent dispensing arm 8. A stepping motor included in the reagent dispensing arm stepping motor section 211 (see FIG. 8) drives the R3 reagent dispensing arm 8 to rotate and also to move in the up/down directions (i.e., the vertical directions). By means of the pipette 8a, the R3 reagent dispensing arm 8 aspirates the R3 reagent that is set in the reagent setting part 16. The R3 reagent dispensing arm 8 dispenses (i.e., discharges), by means of the pipette 8a, the aspirated R3 reagent into the cuvette that is moved from the primary BF separator 11 to the reaction part 9.

When the cuvette that contains the R3 reagent and the sample for which the primary BF separator 11 has performed the B/F separation is moved by a catcher (not shown) from the reaction part 9 to the secondary BF separator 12, the secondary BF separator 12 separates the R3 reagent that is unreacted (i.e., an unnecessary component) from magnetic particles in the sample contained in the cuvette (i.e., B/F separation).

The R4/R5 reagent feeder 15 dispenses, by means of a tube which is not shown, the R4 reagent and the R5 reagent sequentially into the cuvette that contains the sample for which the secondary BF separator 12 has performed the B/F separation.

The detector 14 obtains, by means of a photo multiplier tube, light that is generated in a reaction process between the luminescent substrate (R5 reagent) and the labeled antibody (R3 reagent) that is bound to an antigen in the sample on which the above-described predetermined processes have been performed, thereby measuring the amount of the antigen contained in the sample.

A cover 161 having a round shape is provided above the reagent setting part 16 so as to cover both the reagent setting part 16 and the reaction part 9. The cover 161 has openings formed at predetermined positions through which the R1 to R3 reagent dispensing arms aspirate reagents, move cuvettes, and dispense reagents.

Figure 3:
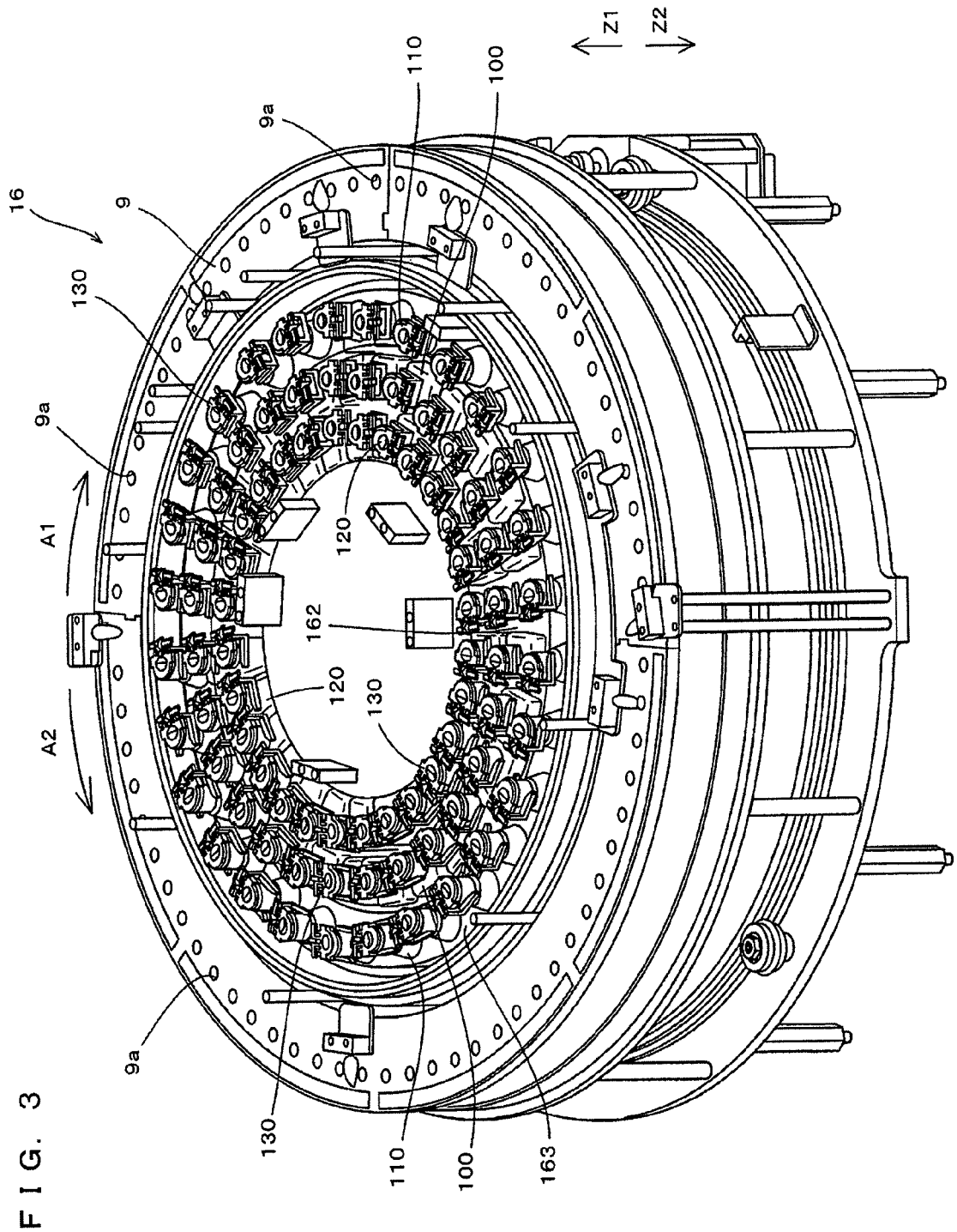
FIG. 3 is a perspective view of a reagent setting part according to the embodiment, which is seen without a cover thereof.

FIG. 3 is a perspective view of the reagent setting part 16 seen without the cover 161. Seen from above, the reagent setting part 16 includes an inner table 162 and an outer table 163 which are both annular tables.

The inner table 162 includes multiple holders configured to hold R1 reagent containers 100 each for containing the R1 reagent and multiple holders configured to hold R3 reagent containers 120 each for containing the R3 reagent. As shown in FIG. 3, these holders hold the R1 reagent containers 100 such that the R1 reagent containers 100 are arranged on the inner table 162 in an annular manner so as to surround the R3 reagent containers 120 which are also arranged on the inner table 162 in an annular manner. As described below, the R1 reagent containers 100 held on the inner table 162 are arranged such that they are adjacent, in a radial direction, to the R3 reagent containers 120 held on the inner table 162, respectively.

The inner table 162 is configured to be horizontally rotatable in the clockwise direction (the arrow A1 direction) and in the counterclockwise direction (the arrow A2 direction). Specifically, the inner table 162 is configured to rotate by means of a first stepping motor 162a (see FIG. 8). When the inner table 162 rotates, the R1 reagent containers 100 and the R3 reagent containers 120 rotate in the same direction by the same angle.

The outer table 163 includes multiple holders configured to hold R2 reagent containers 110 each for containing the R2 reagent. As shown in FIG. 3, these holders hold the R2 reagent containers 110 such that the R2 reagent containers 110 are arranged on the outer table 163 in an annular manner so as to surround the R1 reagent containers 100 which are also arranged in an annular manner.

The outer table 163 is configured to be horizontally rotatable in the clockwise direction (the arrow A1 direction) and in the counterclockwise direction (the arrow A2 direction). Specifically, the outer table 163 is configured to rotate by means of a second stepping motor 163a (see FIG. 8). The outer table 163 is rotatable independently of the inner table 162. The outer table 163 has a function of rotating, thereby agitating the R2 reagent contained in each R2 reagent container 110 held by the outer table 163.

Figure 8:
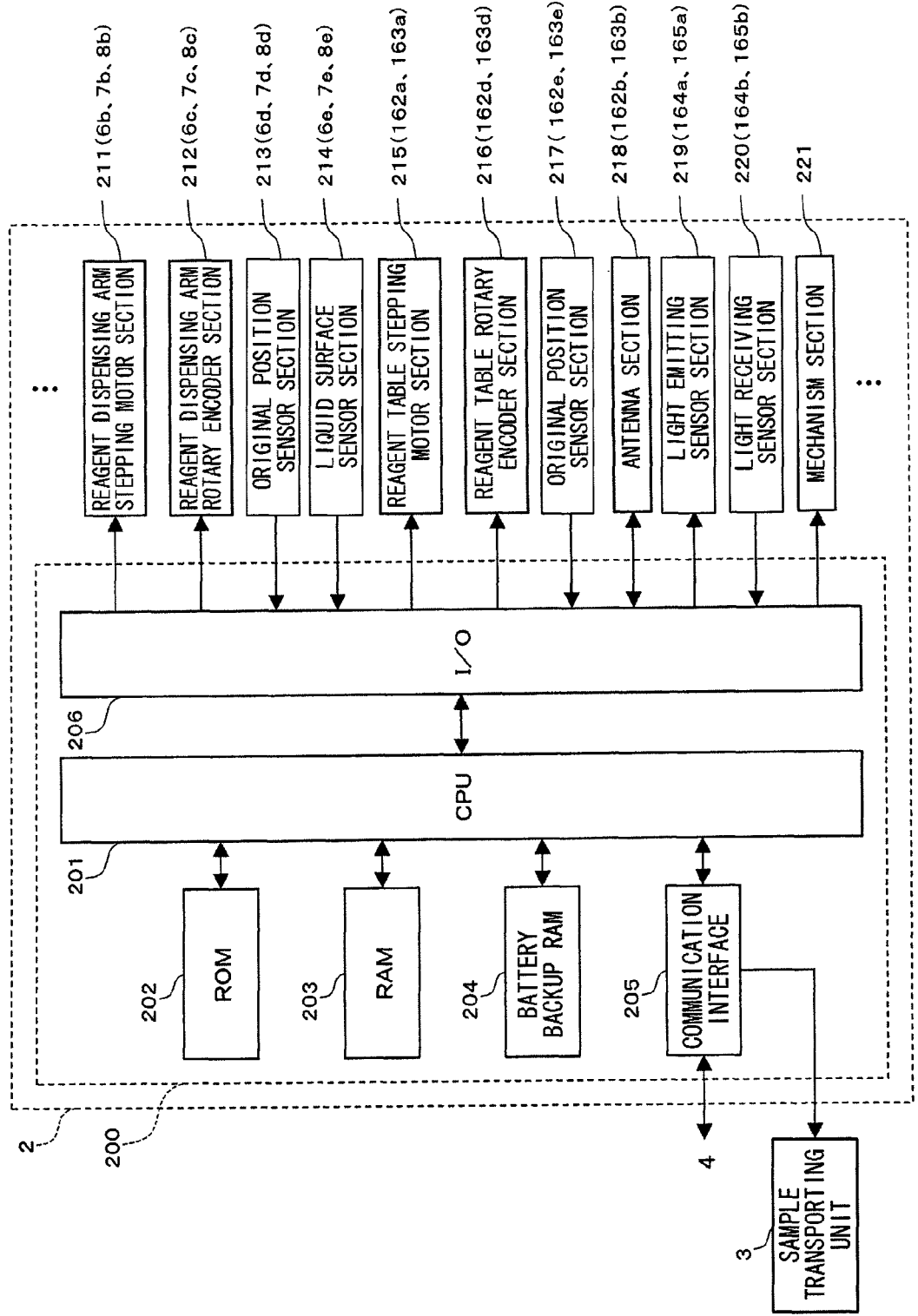
FIG. 8 shows a circuit configuration of the measurement mechanism unit according to the embodiment.

An antenna 162b is disposed inward from the inner table 162 and an antenna 163b is disposed outward from the outer table 163 (see FIG. 8). Each of the antennas reads unique information and reagent management information from, and writes unique information and reagent management information into, an RFID tag, which will be described below. The manner in which the antennas 162b and 163b are disposed will be described below with reference to FIG. 6.

Figure 4:
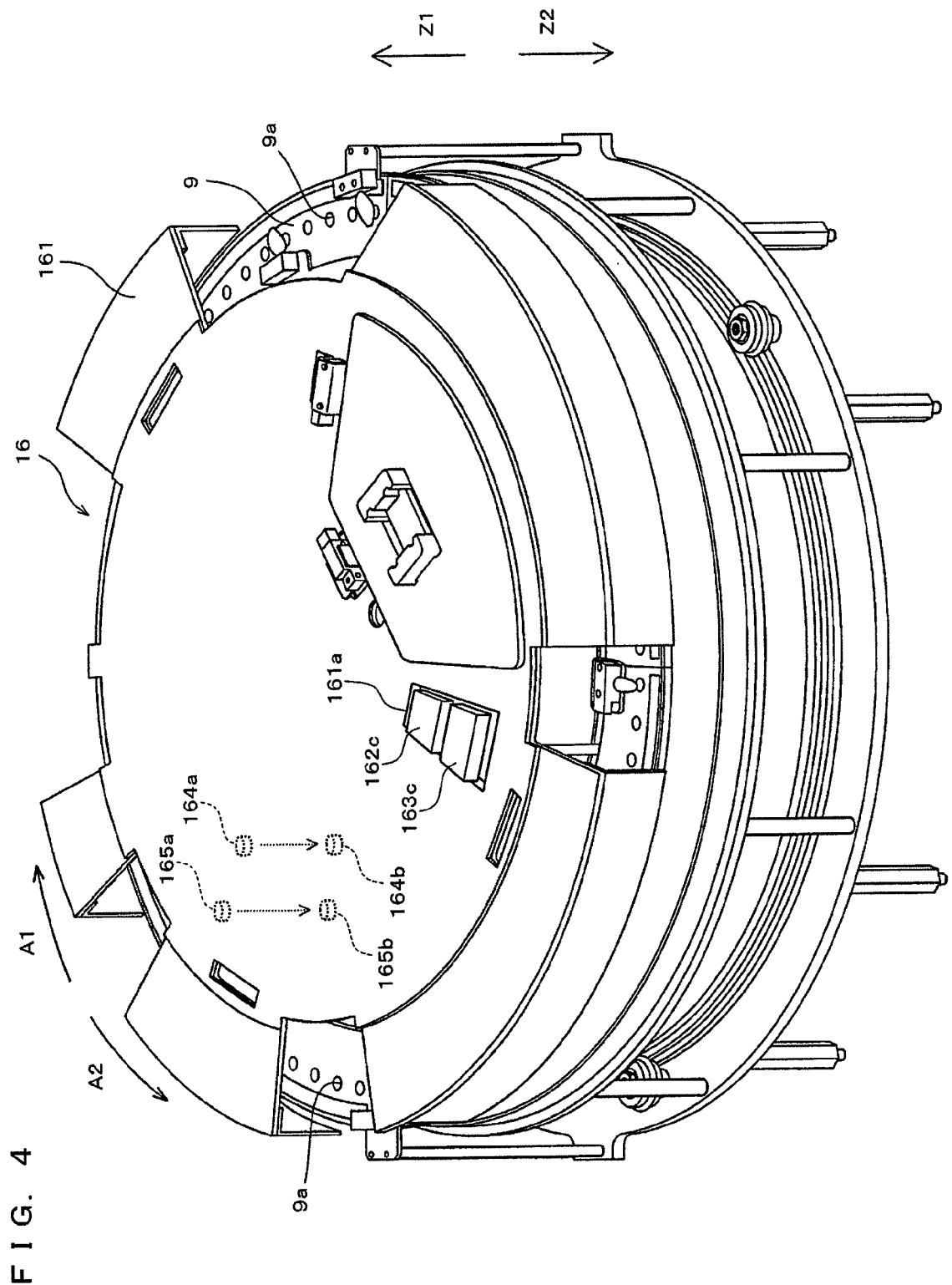
FIG. 4 is a perspective view of the reagent setting part according to the embodiment, which is seen with the cover.

FIG. 4 is a perspective view of the reagent setting part 16 with the cover 161.

As shown in FIG. 4, an insertion/removal hole 161a is formed in the cover 161. The insertion/removal hole 161a allows R1 to R3 reagent containers to be set on the inner table 162 and the outer table 163 from the outside. A reagent container stand 162c and a reagent container stand 163c are disposed immediately below the insertion/removal hole 161a. The reagent container stands 162c and 163c are movable in the vertical directions. The reagent container stands 162c and 163c are configured to be movable within a range between the height of the cover 161 and the height of the inner table 162 and outer table 163.

The structure, in which the insertion/removal hole 161a and the reagent container stands 162c and 163c are configured as above, allows the user to perform, at the outside (i.e., above) the cover 161, an operation for setting R1 to R3 reagent containers on the inner table 162 and the outer table 163 or an operation for removing R1 to R3 reagent containers from the inner table 162 and the outer table 163. To be specific, when an R1 reagent container 100 and an R3 reagent container 120 are mounted on the reagent container stand 162c which is located as shown in FIG. 4 at the height of the cover 161 (or when an R2 reagent container 110 is mounted on the reagent container stand 163c which is located as shown in FIG. 4 at the height of the cover 161) and the reagent container stand 162c (or 163c) is moved downward, the R1 and R3 reagent containers are set on the inner table 162 (or the R2 reagent container is set on the outer table 163), accordingly. The R1 reagent container 100 and the R3 reagent container 120 set on the inner table 162 (or the R2 reagent container 110 set on the outer table 163) are, when the reagent container stand 162c (or 163c) is moved upward, moved to the outside and above the cover 161. In this manner, setting or removal of R1 to R3 reagent containers can be performed.

As shown in FIG. 4, light emitters 164a and 165a of a transmission sensor are disposed at the back-face side of the cover 161. Light receivers 164b and 165b of the transmission sensor are disposed at the reagent setting part 16, below the inner table 162 and the outer table 163. Light emitted from the light emitter 164a and light emitted from the light emitter 165a are received by the light receiver 164b and the light receiver 165b, respectively. Each of the holders of the inner table 162 and the outer table 163 has an opening (not shown) which vertically extends therethrough. Accordingly, when holders that are holding an R1 reagent container 100 and an R3 reagent container 120, which are fitted together as described below, are located between the light emitter 164a and the light receiver 164b, it is determined that the holders are holding the R1 reagent container 100 and the R3 reagent container 120, which are fitted together, since the R1 reagent container 100 and the R3 reagent container 120 block the light emitted from the light emitter 164a. Also, when a holder that is holding an R2 reagent container 110 is located between the light emitter 165a and the light receiver 165b, it is determined that the holder is holding the R2 reagent container 110 since the R2 reagent container 110 blocks the light emitted from the light emitter 165a.

FIG. 5 is a perspective view showing structures of an R1 reagent container 100, an R2 reagent container 110, and an R3 reagent container 120. For the purpose of facilitating the understanding, a cover attached to each reagent container is not shown in FIG. 5.

Referring to (a) of FIG. 5, a container body 101 of the R1 reagent container 100 includes, at its upper side, a cylindrical part 102 which is formed in a substantially cylindrical shape, and at its lower side, a reagent accommodating part 103 for containing a reagent. A round opening 102a is formed at the top end of the cylindrical part 102, and a pair of notch grooves 102b extending horizontally are formed at the side of the cylindrical part 102 in a symmetrical manner. A cover (not shown) is attached to the cylindrical part 102 of the container body 101 via a support member (not shown) which engages with the notch grooves 102b.

As shown in (a) of FIG. 5, a notch 103a is formed at one of two sides of the reagent accommodating part 103, which two sides correspond to the positions, of the cylindrical part 102, where the notch grooves 102b are formed. The notch 103a extends downward (in an arrow Z2 direction) from the top face of the reagent accommodating part 103. The notch 103a is formed such that a protrusion 123a, which will be described below, of the R3 reagent container 120 fits in the notch 103a. By fitting the protrusion 123a of the R3 reagent container 120 in the notch 103a of the R1 reagent container 100, the R1 reagent container 100 and the R3 reagent container 120 can be easily arranged such that they are adjacent to each other with a predetermined interval therebetween.

As shown in (a) of FIG. 5, an RFID (Radio Frequency Identification) tag 104 and a bar code label 105 are affixed to a side of the reagent accommodating part 103 that is the opposite side to the side at which the notch 103a is formed. Unique information and reagent management information are written in the RFID tag 104. The unique information and the reagent management information are read from, or written into, the RFID tag 104 by the antenna 162b via radio waves, which will be described below. The reagent management information is also written on the bar code label 105. The reagent management information written on the bar code label 105 is read by the bar code reader 17. The unique information and the reagent management information will be described below with reference to FIG. 7.

Referring to (b) of FIG. 5, a container body 111 of the R2 reagent container 110 has substantially the same structure as that of the R1 reagent container 100. That is, similar to the R1 reagent container 100, an RFID tag 114 and a bar code label 115 are affixed to a reagent accommodating part 113 of the R2 reagent container 110. Unique information and reagent management information are written in the RFID tag 114. The unique information and the reagent management information are read from, or written into, the RFID tag 114 by the antenna 163b via radio waves, which will be described below. The reagent management information is also written on the bar code label 115. The reagent management information written on the bar code label 115 is read by the bar code reader 17. It should be noted that unlike the R1 reagent container 100 having the notch 103a formed thereon, such a notch is not formed on the reagent accommodating part 113. A cylindrical part 112 of the R2 reagent container 110 has an opening 112a, and a pair of notch grooves 112b are formed at the side of the cylindrical part 112.

Referring to (c) of FIG. 5, a container body 121 of the R3 reagent container 120 has substantially the same structure as that of the R1 reagent container 100. A cylindrical part 122 of the R3 reagent container 120 has an opening 122*a*, and a pair of notch grooves 122*b* are formed at the side of the cylindrical part 122. As shown in (c) of FIG. 5, the aforementioned protrusion 123*a* is formed at one of two sides of a reagent accommodating part 123 of the R3 reagent container 120, which two sides correspond to the positions, of the cylindrical part 122, where the notch grooves 122*b* are formed. The protrusion 123*a* extends downward (in the arrow Z2 direction) from the top face of the reagent accommodating part 123. The protrusion 123*a* is formed such that the protrusion 123*a* fits in the above-described notch 103*a* of the R1 reagent container 100.

At the start of using the R1 reagent container 100 and the R3 reagent container 120, the user always fits the R1 reagent container 100 and the R3 reagent container 120 together via the notch 103*a* and the protrusion 123*a* and then sets them in the holders of the inner table 162. The R1 reagent container 100 and the R3 reagent container 120 are always used in the same measurement. Considering such usage, it is not necessary to separately identify the R3 reagent container 120. Therefore, an RFID tag and a bar code label are not affixed to the R3 reagent container 120. Accordingly, the R1 reagent container 100 and the R3 reagent container 120 fitted together are identified based on the reagent management information read from the RFID tag and the bar code label which are affixed to the R1 reagent container 100 (hereinafter, the R1 reagent container 100 and the R3 reagent container 120 fitted together will be referred to as an "R1/R3 reagent container").

Figure 6:
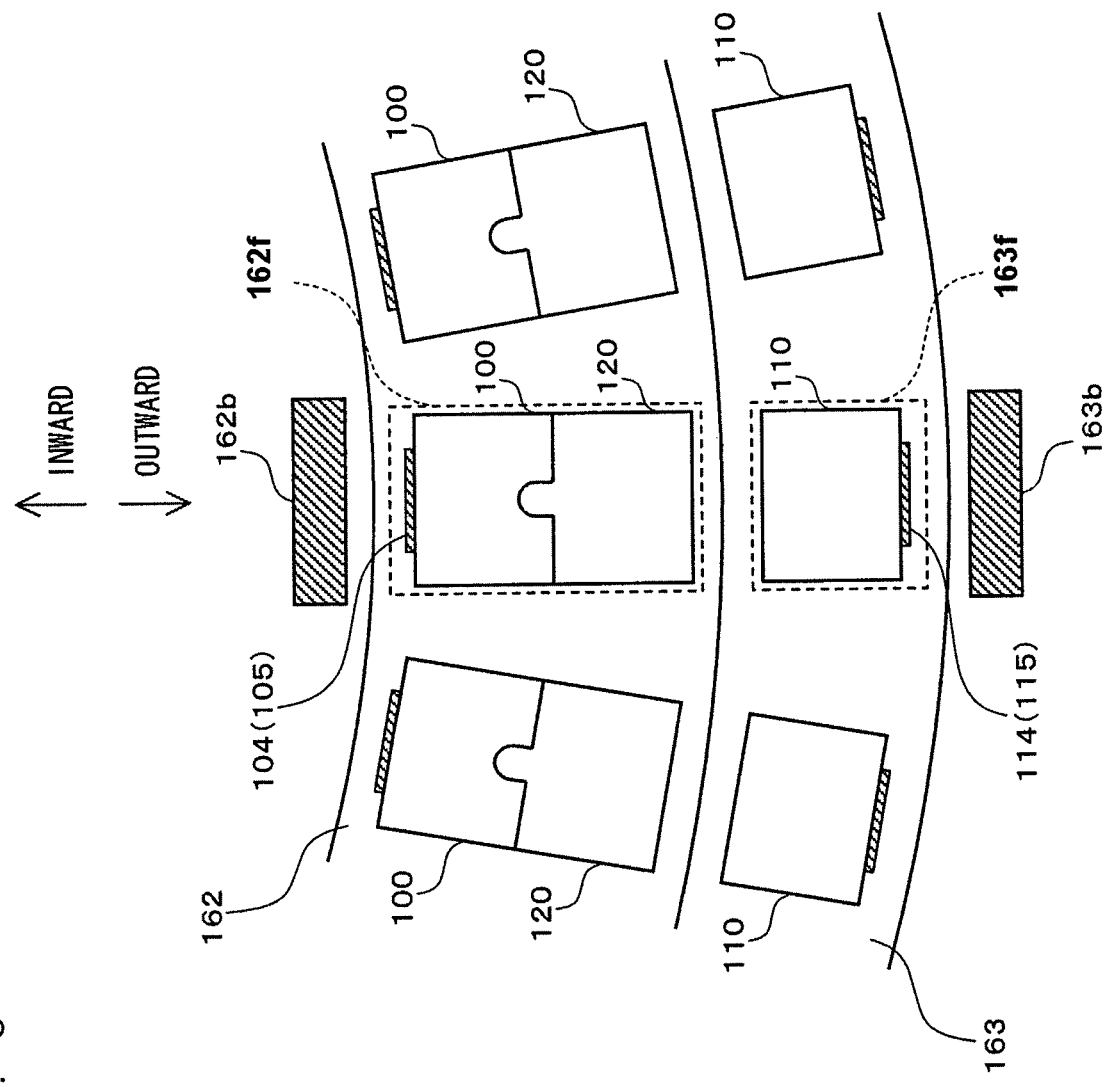
FIG. 6 is a plan view schematically showing an area encompassing antennas according to the embodiment, which is seen from above.

FIG. 6 is a plan view schematically showing an area encompassing the antennas 162*b* and 163*b*, which is seen from above.

As shown in FIG. 6, the antennas 162*b* and 163*b* are disposed in the reagent setting part 16. The antenna 162*b* is disposed inward from the inner table 162 and the antenna 163*b* is disposed outward from the outer table 163. By wireless communication via radio waves, the antenna 162*b* writes reagent management information into, and reads reagent management information from, the RFID tag 104 of the R1/R3 reagent container when the R1/R3 reagent container is located at a position, on the inner table 162, at which the R1/R3 reagent container faces the antenna 162*b* (i.e., a read/write position 162O. As described above, the RFID tag 104 of the R1/R3 reagent container is affixed to the R1 reagent container 100. Also, by wireless communication via radio waves, the antenna 163*b* writes reagent management information into, and reads reagent management information from, the RFID tag 114 of the R2 reagent container 110 when the R2 reagent container 110 is located at a position, on the outer table 163, at which the R2 reagent container 110 faces the antenna 163*b* (i.e., a read/write position 163O.

In a case where the reagent management information in the RFID tag 104 (or 114) is unreadable, the bar code label 105 (or 115) is used instead. That is, if the RFID tag 104 (or 114) is not read by the antenna 162*b* (or 163*b*) since the RFID tag is, for example, damaged, then the user removes from the reagent setting part 16 the reagent container to which the damaged RFID tag is affixed, and reads bar code information from the bar code label of the reagent container by using the handheld bar code reader 17 which is connected to the control apparatus 4. Accordingly, even if the RFID tag is unreadable, the reagent container to which the RFID tag is affixed can be identified.

Figure 7:
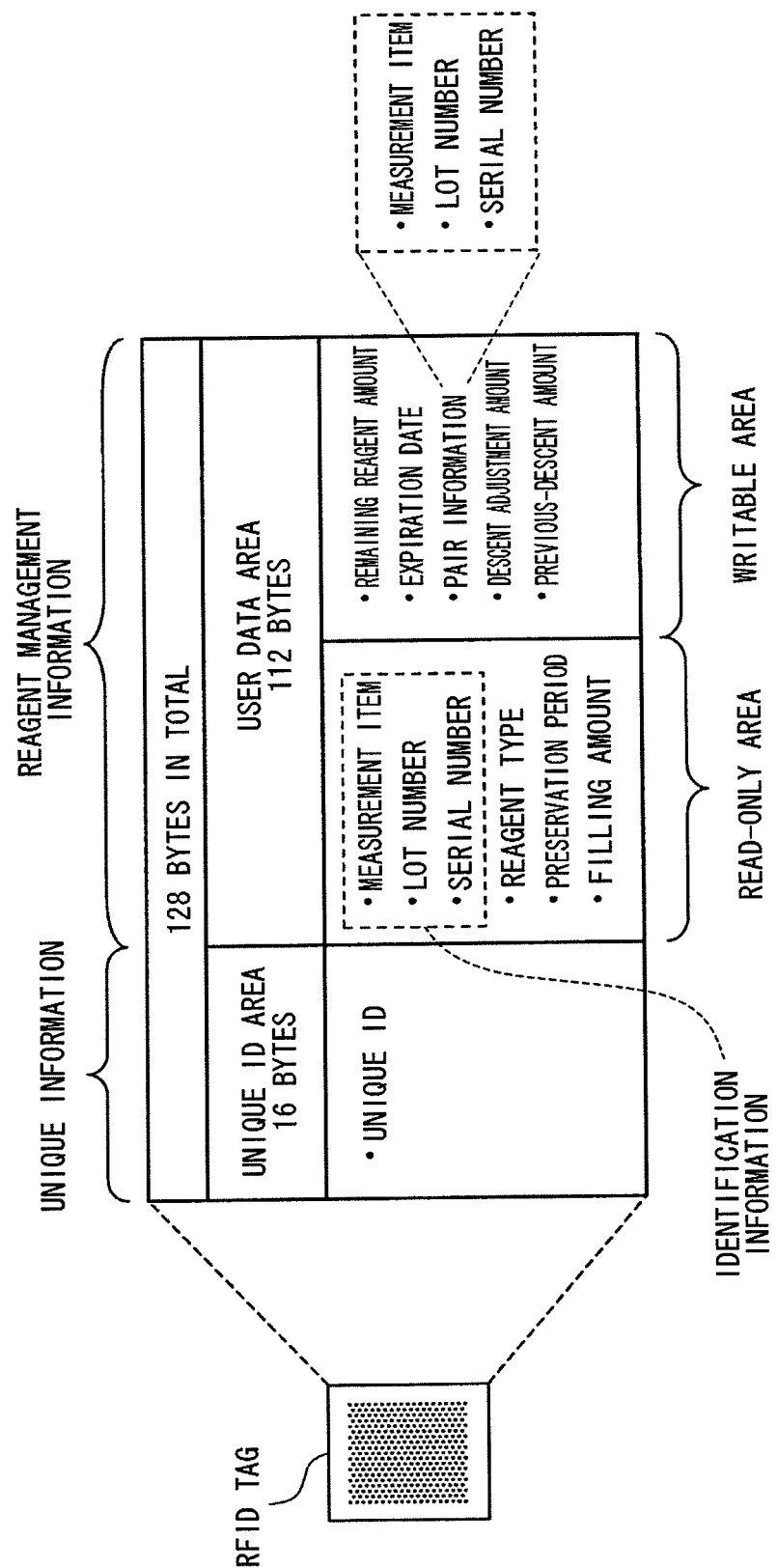
FIG. 7 is a conceptual diagram showing unique information and reagent management information which are stored in an RFID tag according to the embodiment.

FIG. 7 is a conceptual diagram showing unique information and reagent management information which are stored in each of the RFID tag 104 and the RFID tag 114.

As shown in FIG. 7, each of the RFID tag 104 and the RFID tag 114 is configured to store information of 128 bytes. Of the storage capacity of 128 bytes, 16 bytes are allocated for a unique ID area which indicates unique information, and 112 bytes are allocated for a user data area which indicates reagent management information. The unique ID area stores a unique ID for identifying a corresponding RFID tag, and is a read-only storage area. The user data area allows the user to freely write information therein. The user data area includes an area from which data stored therein is readable but into which data is not writable (i.e., a read-only area), and an area from which data stored therein is readable and into which data is writable (i.e., a writable area).

The read-only area stores a measurement item, a lot number, a serial number, a reagent type, a preservation period, and a filling amount. In the writable area, a remaining reagent amount, an expiration date, pair information, a descent adjustment amount, and a previous-descent amount are written. When a reagent container is set on the inner table 162 or the outer table 163 for the first time, there is no information written in the writable area of the RFID tag affixed to the reagent container. It should be noted that the bar code label 105 (or 115) stores information that is the same as the information stored in the read-only area of the RFID tag 104 (or 114).

In the RFID tag (both 104 and 114), the measurement item indicates a measurement item, the measurement of which uses the reagent contained in the reagent container to which the RFID tag is affixed. R1/R3 reagent containers and R2 reagent containers 110 are each uniquely identified by its measurement item, lot number, and serial number (hereinafter, referred to as "identification information"). The serial number allows the corresponding reagent container to be uniquely identified among other reagent containers for which the same measurement item and the same lot number are set. An R1/R3 reagent container and an R2 reagent container 110 that share the same measurement item and the same lot number are packed together and provided to the user. Due to the nature of usage of R1/R3 reagent containers and R2 reagent containers 110, each R1/R3 reagent container is used in combination with (i.e., paired with) an R2 reagent container 110 for which the same measurement item and the lot number as those of the R1/R3 reagent container are set.

In the RFID tag, the reagent type indicates whether the reagent container to which the RFID tag is affixed is an R1/R3 reagent container or an R2 reagent container 110. The preservation period indicates until when the reagent in the reagent container can be preserved. The filling amount indicates the total number of times measurement can be performed by using the reagent. The remaining reagent amount indicates how many more times the measurement can be performed by using the reagent. The expiration date indicates until when the reagent can be used. The expiration date is set when the reagent starts being used.

In the RFID tag, the identification information about a reagent container that is paired with the reagent container to which the RFID tag is affixed is written in the item of pair information. Thus, for example, in the RFID tag 104 affixed to an R1/R3 reagent container that is set on the inner table 162 for the first time, the identification information in the RFID tag 114 affixed to an R2 reagent container 110 that is used in combination with (i.e., paired with) the R1/R3 reagent container is written into the item of pair information. Similarly, in the RFID tag 114 affixed to an R2 reagent container 110 that is set on the outer table 163 for the first time, the identification information in the RFID tag 104 affixed to an R1/R3 reagent container that is used in combination with (i.e., paired with) the R2 reagent container 110 is written into the item of pair information.

In the RFID tag, the descent adjustment amount that is inherent in a sample analyzer in which the reagent container to which the RFID tag is affixed was previously set is written in the item of descent adjustment amount. In the item of previous-descent amount, the number of pulses is written that corresponds to a distance by which a pipette moved, in a previously performed operation of aspirating the reagent from the reagent container, from the original position of the pipette to the liquid surface of the reagent. The descent adjustment amount and the previous-descent amount will be described below with reference to FIG. 10 and FIG. 11. It should be noted that, as described above, an R1 reagent container 100 and an R3 reagent container 120 are fitted together and then used in the same measurement. Therefore, the same unique information and reagent management information are shared by the R1 reagent container 100 and the R3 reagent container 120, and they are written in the RFID tag 104 of the R1/R3 reagent container. However, the RFID tag 104 of the R1/R3 reagent container stores the descent adjustment amount and the previous-descent amount about the R1 reagent and the descent adjustment amount and the previous-descent amount about the R3 reagent, separately.

FIG. 8 shows a circuit configuration of the measurement mechanism unit 2.

The measurement mechanism unit 2 includes: the controller 200; the reagent dispensing arm stepping motor section 211; a reagent dispensing arm rotary encoder section 212; an original position sensor section 213; a liquid level sensor section 214; a reagent table stepping motor section 215; a reagent table rotary encoder section 216; an original position sensor section 217; an antenna section 218; a light emitting sensor section 219; a light receiving sensor section 220; and a mechanism section 221. The controller 200 includes a CPU 201, a ROM 202, a RAM 203, a battery backup RAM 204, a communication interface 205, and an I/O interface 206.

The CPU 201 executes computer programs stored in the ROM 202 and computer programs loaded into the RAM 203. The RAM 203 is used for loading computer programs stored in the ROM 202, and is also used as a work area for the CPU 201 at the time of executing these computer programs. The RAM 203 stores a database. In the database, pieces of reagent management information about reagent containers that are held by the holders of the inner table 162 and the outer table 163 are registered in association with the respective holders (hereinafter, referred to as a "reagent DB"). The battery backup RAM 204 is configured such that even when the measurement mechanism unit 2 is powered off, the data stored in the RAM 204 is not deleted. As described below, the battery backup RAM 204 stores the descent adjustment amount for each of the R1 to R3 reagents set in the measurement mechanism unit 2.

The communication interface 205 is connected to the sample transporting unit 3 and the control apparatus 4. Via the communication interface 205, the CPU 201 transmits optical information about a sample (i.e., data of the amount of light generated by the reaction between the labeled antibody and the luminescent substrate) to the control apparatus 4 and receives signals from the control apparatus 4. The CPU 201 transmits an instruction signal to the sample transporting unit 3 via the communication interface 205 to drive the sample transporting unit 3.

The CPU 201 is connected via the I/O interface 206 to the reagent dispensing arm stepping motor section 211, the reagent dispensing arm rotary encoder section 212, the original position sensor section 213, the liquid level sensor section 214, the reagent table stepping motor section 215, the reagent table rotary encoder section 216, the original position sensor section 217, the antenna section 218, the light emitting sensor section 219, the light receiving sensor section 220, and the mechanism section 221.

The reagent dispensing arm stepping motor section 211 includes stepping motors 6b, 7b, and 8b for driving the R1, R2, and R3 reagent dispensing arms to move in the vertical directions, respectively. The reagent dispensing arm rotary encoder section 212 includes rotary encoders 6c, 7c, and 8c which are included in the stepping motors 6b, 7b, and 8b, respectively. Each of the rotary encoders 6c, 7c, and 8c is configured to output the number of pulses that corresponds to the amount of rotational displacement of a corresponding one of the stepping motors 6b, 7b, and 8b. By counting the numbers of pulses outputted from the respective rotary encoders 6c, 7c, and 8c, rotation amounts of the respective stepping motors 6b, 7b, and 8b can be detected.

The reagent dispensing arm stepping motor section 211 also includes stepping motors for driving the respective R1 to R3 reagent dispensing arms to rotate. Accordingly, the reagent dispensing arm rotary encoder section 212 includes rotary encoders which are included in these stepping motors, respectively.

The original position sensor section 213 includes transmission sensors 6d, 7d, and 8d each for detecting that a corresponding one of the R1, R2, and R3 reagent dispensing arms is located at its predetermined position along the vertical direction (i.e., original position). Each of the transmission sensors 6d, 7d, and 8d includes a light emitter and a light receiver. When the R1, R2, and R3 reagent dispensing arms are located at their predetermined positions along the vertical direction, the light emitted from the light emitters of the respective transmission sensors 6d, 7d, and 8d is blocked and the light does not fall on the light receivers of the respective transmission sensors 6d, 7d, and 8d. Accordingly, it is detected that the R1 to R3 reagent dispensing arms are located at their original positions along the vertical direction, that is, it is detected that the pipettes 6a, 7a, and 8a are located at their original positions along the vertical direction.

The original position sensor section 213 also includes transmission sensors each for detecting that a corresponding one of the R1, R2, and R3 reagent dispensing arms is located at its predetermined rotational position (i.e., original position).

The liquid level sensor section 214 includes liquid level sensors 6e, 7e, and 8e which are included in the pipettes 6a, 7a, and 8a of the R1, R2 and R3 reagent dispensing arms, respectively. When any one of the pipettes 6a, 7a, and 8a comes into contact with a liquid surface, the corresponding one of the liquid level sensors 6e, 7e, and 8e electrically detects the contact.

The reagent table stepping motor section 215 includes the first stepping motor 162a and the second stepping motor 163a. The reagent table rotary encoder section 216 includes a rotary encoder 162d and a rotary encoder 163d which are included in the first stepping motor 162a and the second stepping motor 163a, respectively. Each of the rotary encoder 162d and the rotary encoder 163d is configured to output the number of pulses in accordance with the amount of rotational displacement of a corresponding one of the first stepping motor 162a and the second stepping motor 163a.

The original position sensor section 217 includes a transmission sensor 162e for detecting that the first stepping motor 162a is located at its predetermined rotational position (i.e., original position), and includes a transmission sensor 163e for detecting that the second stepping motor 163a is located at its predetermined rotational position (i.e., original position).

The antenna section 218 includes the antennas 162b and 163b. The CPU 201 controls the antennas 162b and 163b to read reagent management information from the RFID tag 104 and the RFID tag 114, respectively. The reagent management information read by the antennas 162b and 163b is outputted to the CPU 201 via the I/O interface 206, and then stored in the reagent DB of the RAM 203. The light emitting sensor section 219 includes the light emitters 164a and 165a. The CPU 201 controls each of the light emitters 164a and 165a to emit light. The light receiving sensor section 220 includes the light receivers 164b and 165b. Detection signals from the light receiving sensor section 220 are outputted to the CPU 201 via the I/O interface 206. The mechanism section 221 includes other mechanisms of the measurement mechanism unit 2, and is driven by the CPU 201 performing control.

Figure 9:
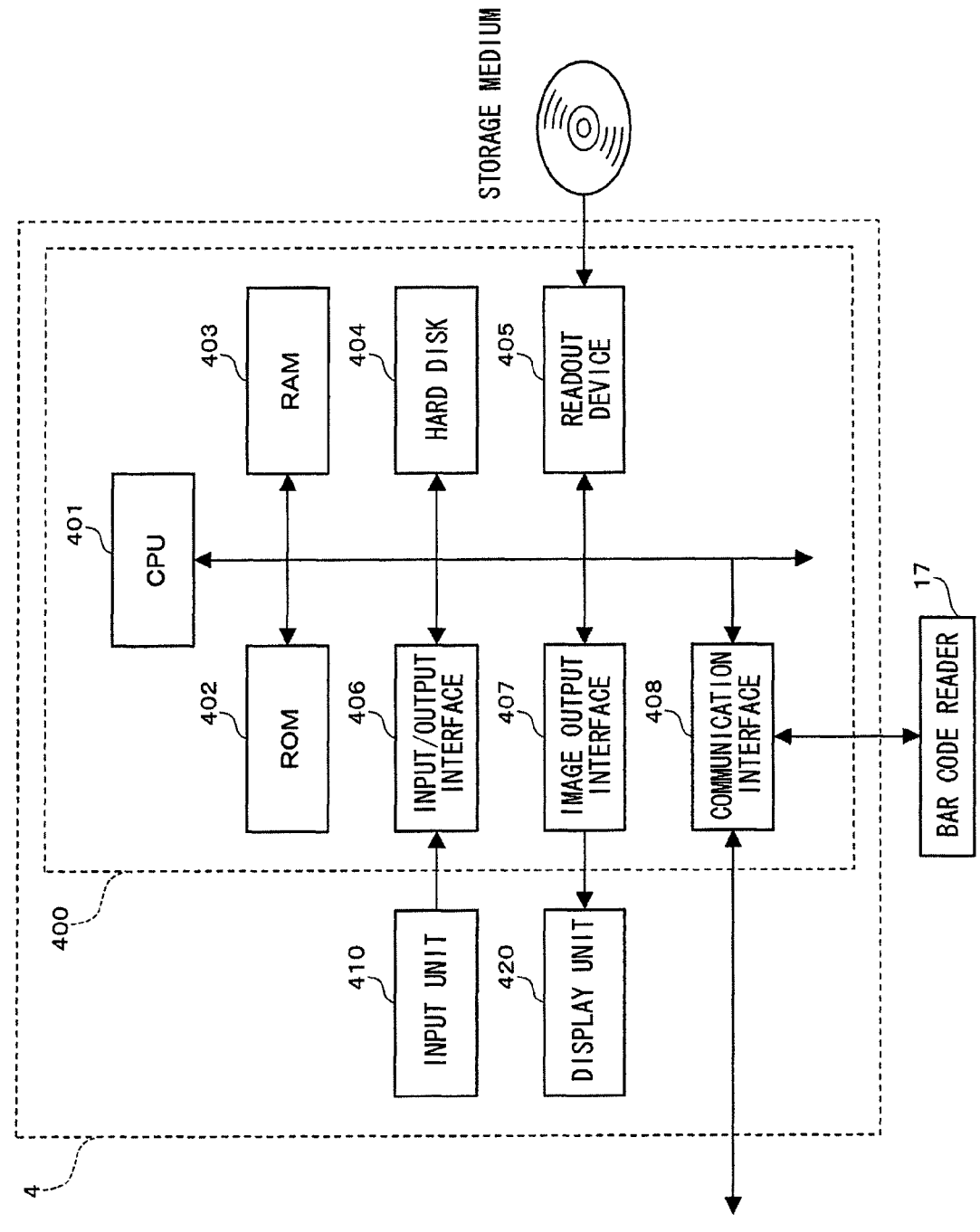
FIG. 9 shows a circuit configuration of a control apparatus according to the embodiment.

FIG. 9 shows a circuit configuration of the control apparatus 4.

The control apparatus 4 is structured as a personal computer. The control apparatus 4 includes the body 400, the input unit 410, and the display unit 420. The body 400 includes a CPU 401, a ROM 402, a RAM 403, a hard disk 404, a readout device 405, an input/output interface 406, an image output interface 407, and a communication interface 408.

The CPU 401 executes computer programs stored in the ROM 402 and computer programs loaded into the RAM 403. The RAM 403 is used for loading computer programs stored in the ROM 402 and the hard disk 404. The RAM 403 is also used as a work area for the CPU 401 at the time of executing these computer programs.

Various computer programs executed by the CPU 401, such as an operating system and application programs, and data used for executing these computer programs, are installed in the hard disk 404. Specifically, a program for performing, for example, a display on the display unit 420 based on the reagent DB which is transmitted from the measurement mechanism unit 2, a program for transmitting an instruction to the measurement mechanism unit 2 based on an instruction received from the user via the input unit 410, and the like are installed in the hard disk 404.

The readout device 405 is structured as a CD drive, DVD drive, or the like. The readout device 405 is configured to read a computer program and data that are stored in a storage medium. The input unit 410, which includes a mouse and a keyboard, is connected to the input/output interface 406. When an operator operates the input unit 410, data is inputted into the control apparatus 4, accordingly. The image output interface 407 is connected to the display unit 420, which includes a display and the like. The image output interface 407 outputs, to the display unit 420, image signals that correspond to image data. The display unit 420 displays an image based on the image signals that are inputted from the image output interface 407. The communication interface 408 enables data transmission to, and data reception from, the measurement mechanism unit 2 and the bar code reader 17.

Figure 10:
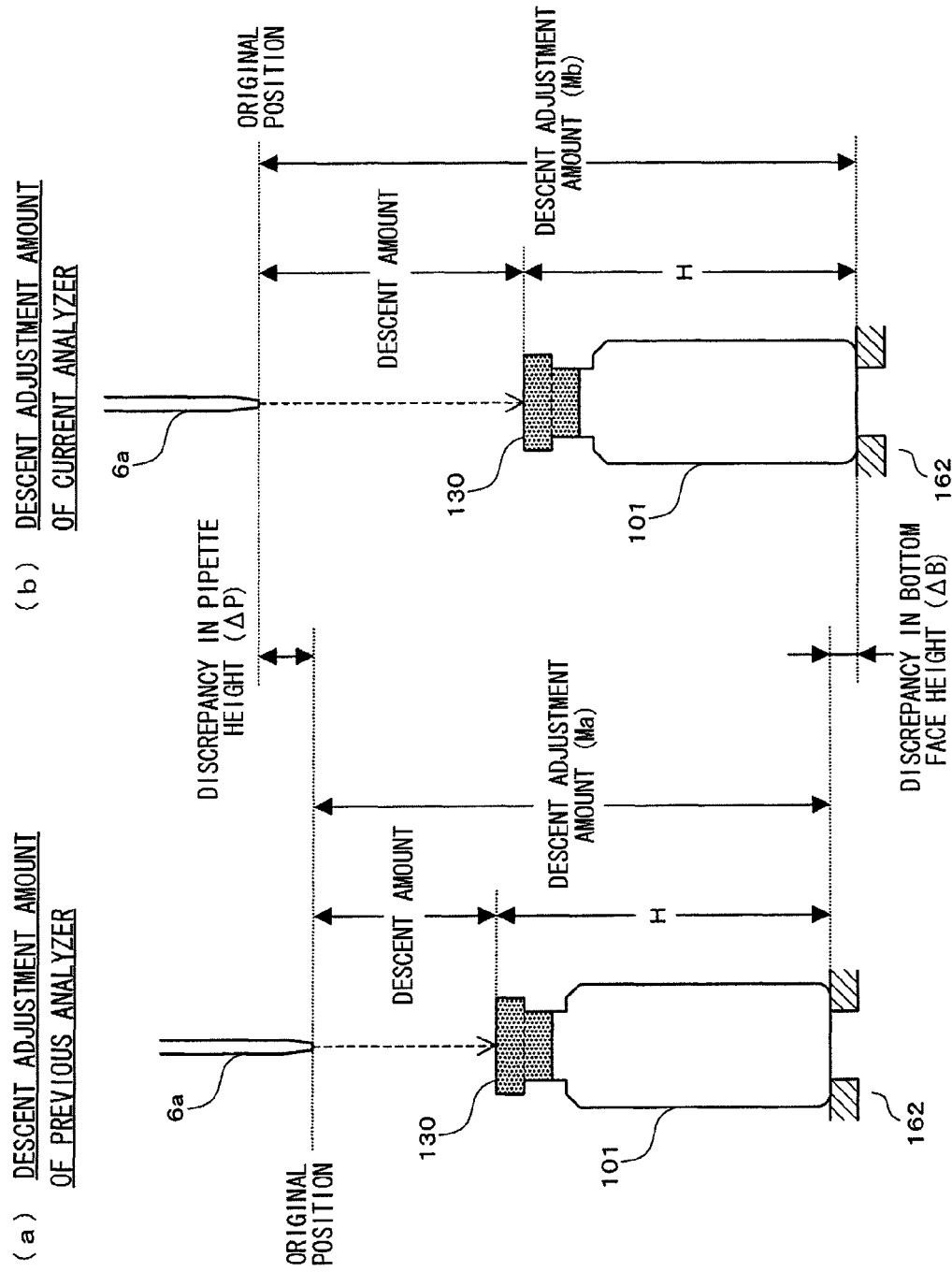
FIG. 10 illustrates a descent adjustment amount according to the embodiment.

FIG. 10 illustrates the descent adjustment amount. The descent adjustment amount is a value inherent in the sample analyzer 1. The descent adjustment amount is measured in advance in the manner described below when the assembling of the measurement mechanism unit 2 is completed.

FIG. 10 shows examples of measurements of the descent adjustment amount that are performed by different measurement mechanism units 2, respectively. For the purpose of facilitating the understanding, (b) of FIG. 10 shows an example of measurement of the descent adjustment amount performed by a measurement mechanism unit 2 in which a reagent container is currently set (hereinafter, this measurement mechanism unit 2 may be referred to as a "current measurement mechanism unit 2"), and in comparison, (a) of FIG. 10 shows an example of measurement of the descent adjustment amount performed by another measurement mechanism unit 2 in which the reagent container was previously set (hereinafter, this measurement mechanism unit 2 may be referred to as a "previous measurement mechanism unit 2"). As mentioned above, these measurements are performed after the respective measurement mechanism units 2 are assembled.

Referring to (a) of FIG. 10, in measuring the descent adjustment amount for the R1 reagent in the measurement mechanism unit 2, the container body 101 of an R1 reagent container 100 that has a metal jig 130 fitted in its top opening is used. A measurer who performs the measurement sets the container body 101 on the inner table 162 in one of the holders for holding R1 reagent containers 100. Next, the measurer sets the R1 reagent dispensing arm 6 to be in its original position along the vertical direction, thereby setting the pipette 6a of the R1 reagent dispensing arm 6 to be in its original position. In this state, a count value, which indicates the number of output pulses of the rotary encoder 6c, is set to 0.

Next, the measurer causes the pipette 6a to slowly descend toward the holder of the inner table 162 that is holding the container body 101. When the liquid level sensor 6e of the pipette 6a detects that the pipette 6a has come in contact with the jig 130, the measurer stops the pipette 6a from descending. At this time, a value (H) is added to the above count value which indicates the number of output pulses of the rotary encoder 6c. The value (H) is a result of converting the length from the top face of the jig 130 to the bottom face of the container body 101 into a count value indicating the number of output pulses of the rotary encoder 6c. In this manner, the descent adjustment amount (Ma) is obtained for the R1 reagent in the measurement mechanism unit 2.

Similar to the case of the R1 reagent, also in each of the cases of the R2 reagent and the R3 reagent, the descent adjustment amount is obtained by causing the corresponding pipette to descend from its original position to the jig fitted to the corresponding container body.

When the descent adjustment amount is obtained for each of the R1 to R3 reagents in the above manner in the measurement mechanism unit 2, these descent adjustment amounts are stored in the battery backup RAM 204 of the measurement mechanism unit 2.

Referring to (b) of FIG. 10, also in the measurement mechanism unit 2 in which the reagent container is currently set, the descent adjustment amount (Mb) is obtained for each of the R1 to R3 reagents in the same manner as the measurement performed by the previous measurement mechanism unit 2. The obtained descent adjustment amounts (Mb) are stored in the battery backup RAM 204 of the current measurement mechanism unit 2.

There is a case where, as shown in FIG. 10, the descent adjustment amounts (Ma) and (Mb) of the two respective measurement mechanism units 2 are different from each other due to, for example, assembly errors of these measurement mechanism units 2. Specifically, it is possible that the descent adjustment amount obtained for the R1 reagent in the previous measurement mechanism unit 2, and the descent adjustment amount obtained for the R1 reagent in the current measurement mechanism unit 2, are different from each other due to discrepancies between these measurement mechanism units 2 in terms of the original position of the pipette 6*a* and the position of the bottom face of the set container body 101.

It should be noted that a difference (Mb−Ma) between the descent adjustment amount (Mb) of the current measurement mechanism unit 2 (i.e., current sample analyzer) and the descent adjustment amount (Ma) of the previous measurement mechanism unit 2 (i.e., previous sample analyzer) is calculated by an equation shown below if discrepancies between the current sample analyzer and the previous sample analyzer are as follows as shown in FIG. 10: a discrepancy in the height of the pipette 6*a* is ΔP; and a discrepancy in the height of the bottom face of the container body 101 is ΔB.

$$Mb-Ma=\Delta P+\Delta B \quad (1)$$

Figure 11:
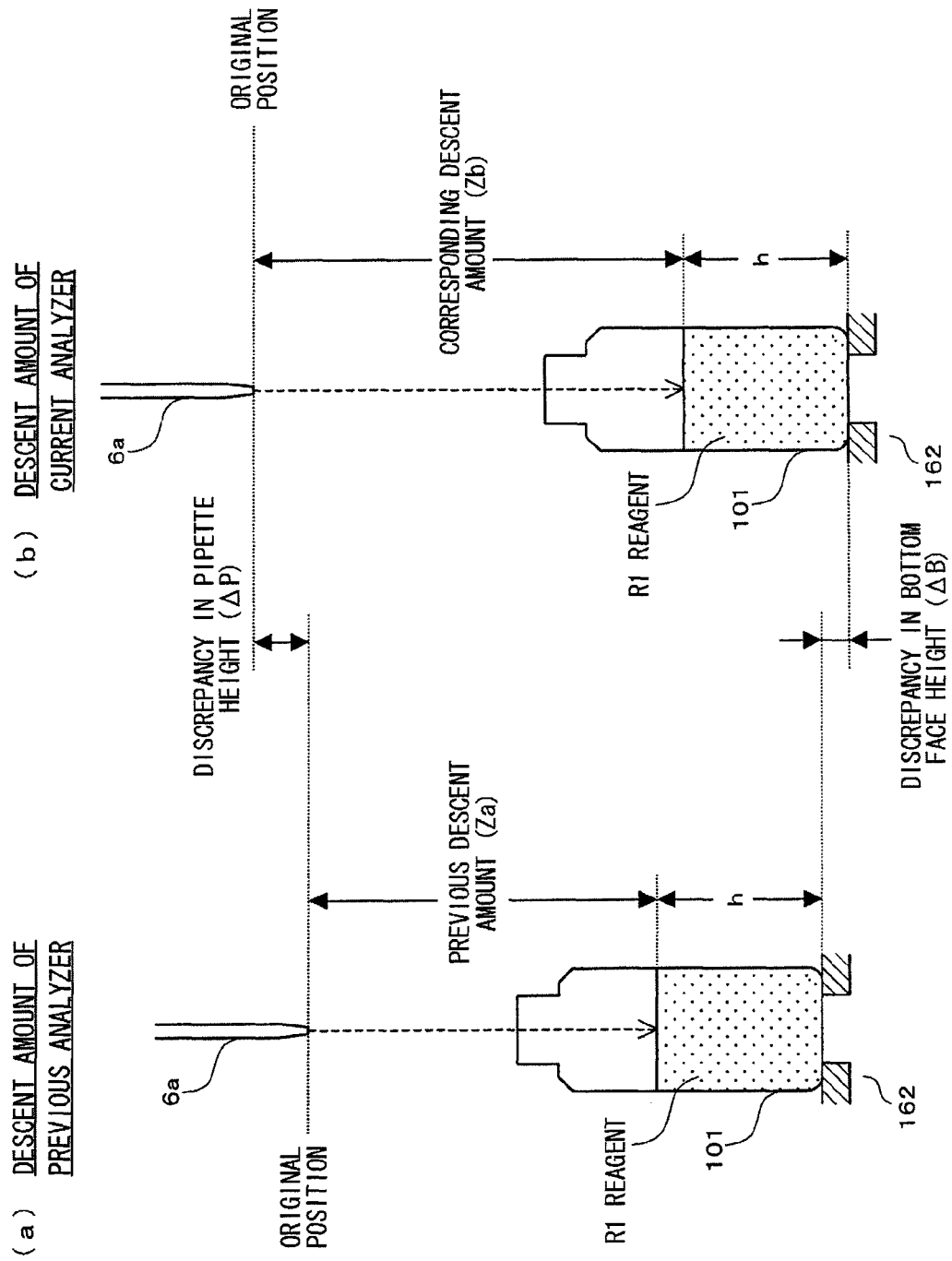
FIG. 11 illustrates descent amounts according to the embodiment.

FIG. 11 illustrates descent amounts. Shown in (a) of FIG. 11 is a descent amount of the pipette 6*a* at the time of aspirating the R1 reagent from an R1 reagent container 100 in the previous measurement mechanism unit 2 shown in (a) of FIG. 10 (i.e., a previous-descent amount). Shown in (b) of FIG. 11 is a descent amount of the pipette 6*a* on the assumption that the R1 reagent container shown in (a) of FIG. 11 is set in the current measurement mechanism unit 2 shown in (b) of FIG. 10 (i.e., a corresponding-descent amount).

Similar to the obtaining of the descent adjustment amount as illustrated in FIG. 10, each of the previous-descent amount and the corresponding-descent amount is obtained from a count value which indicates the number of pulses that are outputted from the rotary encoder 6*c* from when the pipette 6*a* is located at its original position to when the liquid level sensor 6*e* detects the liquid surface of the R1 reagent.

In FIG. 11, assume a case where the length (represented as the number of pulses) from the liquid surface of the R1 reagent to the bottom face of the container body 101 is h. In this case, the length (represented as the number of pulses) from the original position of the pipette 6*a* in (a) of FIG. 11 to the bottom face of the container body 101 is (Za+h) and the length (represented as the number of pulses) from the original position of the pipette 6*a* in (b) of FIG. 11 to the bottom face of the container body 101 is (Zb+h). A difference between (Za+h) and (Zb+h) is calculated by an equation shown below using the discrepancy ΔP (represented as the number of pulses) in the height of the pipette 6*a* and the discrepancy ΔB (represented as the number of pulses) in the height of the bottom face of the container body 101.

$$(Zb+h)-(Za+h)=\Delta P+\Delta B \quad (2)$$

Based on the above equations (1) and (2), the corresponding-descent amount (Zb) is represented by an equation below.

$$Zb=Za+(Mb-Ma) \quad (3)$$

As indicated by the above equation (3), even though there are discrepancies, in terms of the height of the pipette 6*a* and the height of the bottom face of the container body 101, between the previous measurement mechanism unit 2 and the current measurement mechanism unit 2 due to assembly errors or the like, the corresponding-descent amount (Zb) can be obtained by adding the difference (Mb−Ma) between the descent adjustment amounts about the R1 reagent to the previous-descent amount (Za). It should be noted that, also in each of the cases of an R2 reagent container 110 and an R3 reagent container 120, the corresponding-descent amount can be obtained in a similar manner. That is, in the case of an R2 reagent container 110 (or R3 reagent container 120), the corresponding-descent amount can be obtained by adding the difference between the descent adjustment amounts about the R2 reagent (or R3 reagent) to the previous-descent amount about the R2 reagent (or R3 reagent).

As described above, the descent adjustment amounts obtained in the current measurement mechanism unit 2 for the R1 to R3 reagents, respectively, are stored in the battery backup RAM 204 of the current measurement mechanism unit 2, whereas the descent adjustment amount and the previous-descent amount obtained in the previous measurement mechanism unit 2 for each of the R1 to R3 reagents are written into the corresponding RFID tag when aspiration of the reagent has been performed. The previous-descent amount written here is a descent amount required for the pipette to reach the liquid surface prior to the reagent aspiration. Accordingly, a descent amount required for the pipette to reach the actual liquid surface of the reagent (the R1, R2, or R3 reagent for which the reagent aspiration has been performed) is greater than the previous-descent amount written in the RFID tag, by an amount corresponding to the aspirated reagent amount. In the current measurement mechanism unit 2, the corresponding-descent amount is obtained based on the above equation (3) by reading the previous-descent amount and the descent adjustment amount from the RFID tag. The obtained corresponding-descent amount is less than an actual descent amount that is obtained in the current measurement mechanism unit 2 when the reagent liquid surface is detected, by an amount corresponding to the aforementioned aspirated reagent amount.

Figure 12:
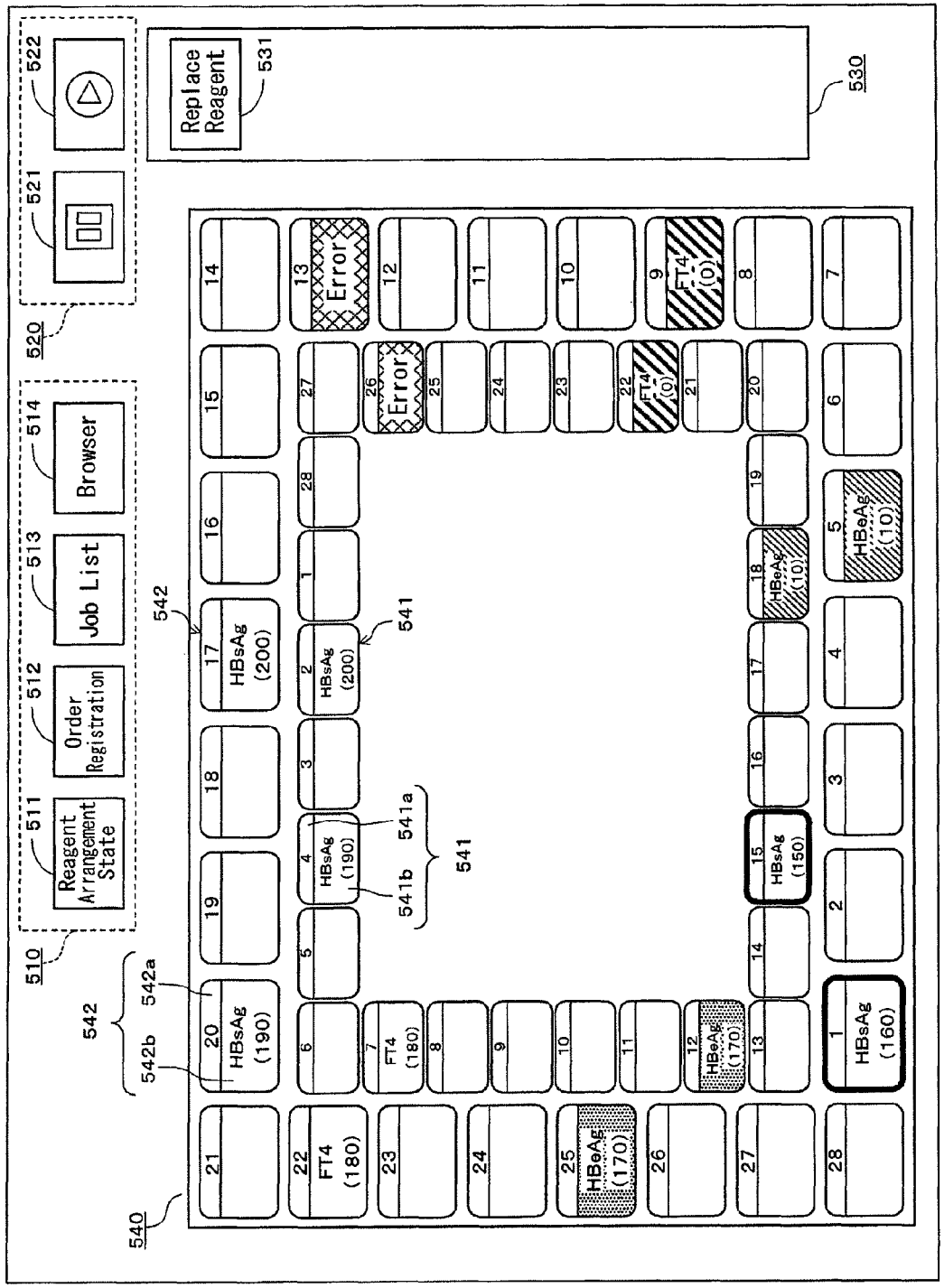
FIG. 12 shows an example of a screen, displayed on a display unit of the control apparatus according to the embodiment, that shows an arrangement state of reagents.

FIG. 12 shows an example of a screen, displayed on the display unit 420 of the control apparatus 4, that shows an arrangement state of reagents. The screen showing the arrangement state of reagents includes a display screen selection area 510, a measurement instruction area 520, an operation instruction area 530, and a reagent arrangement display area 540.

The display screen selection area 510 includes a reagent arrangement state button 511, an order registration button 512, a job list button 513, and a browser button 514. When the reagent arrangement state button 511 is pressed, a screen showing an arrangement state of reagents is displayed (as shown in FIG. 12). When the order registration button 512 is pressed, an order registration screen (not shown) is displayed. The order registration screen includes a screen through which a sample to be measured can be registered. When the job list button 513 is pressed, a list screen (see FIG. 16) that shows the current status and results of measurement is displayed. When the browser button 514 is pressed, a list screen (not shown) that shows measurement results details is displayed.

The measurement instruction area 520 includes a measurement interruption button 521 and a measurement start button 522. When the measurement interruption button 521 is pressed, measurement that is being performed by the measurement mechanism unit 2 is interrupted. When the measurement start button 522 is pressed, the measurement mechanism unit 2 starts performing measurement based on registered orders.

The operation instruction area 530 includes a reagent replacement button 531. When the reagent replacement button 531 is pressed, reagent replacement starts.

In an inward area among the areas within the reagent arrangement display area 540 (hereinafter, simply referred to as an "inward area"), twenty-eight R1/R3 reagent indicia 541 are displayed in an annular manner whereas in an outward area among the areas within the reagent arrangement display area 540 (hereinafter, simply referred to as an "outward area"), twenty-eight R2 reagent indicia 542 are displayed in an annular manner. The R1/R3 reagent indicia 541 correspond to respective R1/R3 reagent containers that are held by the holders of the inner table 162, and the R2 reagent indicia 542 correspond to respective R2 reagent containers 110 that are held by the holders of the outer table 163.

Each of the R1/R3 reagent indicia 541 includes: a position indicating portion 541a for indicating the position of the corresponding holder; and a content indicating portion 541b for indicating the measurement item and the remaining reagent amount that are stored in the RFID tag 104 of the R1/R3 reagent container held by the holder. Similarly, each of the R2 reagent indicia 512 includes: a position indicating portion 542a for indicating the position of the corresponding holder; and a content indicating portion 542b for indicating the measurement item and the remaining reagent amount that are stored in the RFID tag 114 of the R2 reagent container 110 held by the holder.

Among the held reagent containers, if an R1/R3 reagent container and an R2 reagent container are determined to be usable for measurement based on the result of reading their RFID tag 104 and RFID tag 114, then the R1/R3 reagent indicium 541 corresponding to the holder holding the R1/R3 reagent container and the R2 reagent indicium 542 corresponding to the holder holding the R2 reagent container are displayed, for example, in a manner as shown in a holding position (2) in the inward area and a holding position (17) in the outward area. If it is determined by means of the light emitting sensor section 219 and the light receiving sensor section 220 that a reagent container is not set in one of the holders, then the content indicating portion corresponding to the holder is left blank. During measurement, if a liquid surface position error, which will be described below, occurs for a reagent container three times consecutively, then the content indicating portion of the reagent indicium that corresponds to the holder holding the reagent container is displayed, for example, in a manner as shown in a holding position (12) in the inward area and a holding position (25) in the outward area.

Further, if it is determined based on the result of reading the RFID tag 104 or 114 of a reagent container that the reagent container is not paired with any other reagent container, then the R1/R3 reagent indicium 541, or the R2 reagent indicium 542, that corresponds to the holder holding the reagent container is enclosed by a heavy line in a manner as shown in a holding position (15) in the inward area or a holding position (1) in the outward area. If it is determined that the remaining reagent amount of a reagent container is small, then the content indicating portion of the reagent indicium that corresponds to the holder holding the reagent container is shaded by narrowly-spaced diagonal lines in the display in a manner as shown in a holding position (18) in the inward area or a holding position (5) in the outward area. If it is determined that the remaining reagent amount of a reagent container is 0 or the expiration date of the reagent is expired, then the content indicating portion of the reagent indicium that corresponds to the holder holding the reagent container is shaded by widely-spaced diagonal lines in the display in a manner as shown in a holding position (22) in the inward area or a holding position (9) in the outward area. If a reagent container is unusable due to an error in reading the RFID tag 104 or 114 of the reagent container, then the content indicating portion of the reagent indicium that corresponds to the holder holding the reagent container is shaded in a grid-like pattern in the display in a manner as shown in a holding position (26) in the inward area or a holding position (13) in the outward area, and also, a message "error" is shown in the content indicating portion.

FIG. 13 is a flowchart showing a measurement preparation process performed by the measurement mechanism unit 2. The measurement preparation process is performed when the sample analyzer 1 is powered on, for example. It should be noted that the measurement preparation process is performed for the inner table 162 in relation to R1/R3 reagent containers, in parallel with the measurement preparation process that is performed for the outer table 163 in relation to R2 reagent containers 110. Hereinafter, only the measurement preparation process performed for the inner table 162 is described.

First, the CPU 201 of the measurement mechanism unit 2 causes the R1 reagent dispensing arm 6, the R3 reagent dispensing arm 8, and the inner table 162 to move to their original positions (S11). To be specific, the position of the R1 reagent dispensing arm 6 along the vertical direction and the rotational position of the R1 reagent dispensing arm 6, and the position of the R3 reagent dispensing arm 8 along the vertical direction and the rotational position of the R3 reagent dispensing arm 8, are adjusted to be at the original positions by using output signals from the original position sensor section 213. The rotational position of the inner table 162 is adjusted to be at the original position by using an output signal from the transmission sensor 162e of the original position sensor section 217. Next, the CPU 201 causes the inner table 162 to rotate, and checks, by means of the light emitter 164a and the light receiver 164b, whether each of the holders of the inner table 162 is holding an R1/R3 reagent container (S12).

Next, the CPU 201 causes the inner table 162 to rotate, thereby moving an R1/R3 reagent container to the read/write position 162f (S13). Subsequently, the CPU 201 reads, via the antenna 162b, reagent management information from the RFID tag 104 affixed to the R1/R3 reagent container (S14). Based on the read reagent management information about the R1/R3 reagent container, the CPU 201 stores the reagent management information about the R1 reagent container 100 and the reagent management information about the R3 reagent container 120 in the reagent DB of the RAM 203 in association with the holder holding the R1 reagent container 100 and the holder holding the R3 reagent container 120, separately (S15). In this manner, the same reagent management information shared by the R1 reagent container 100 and the R3 reagent container 120 is stored in the reagent DB as the reagent management information about the R1 reagent container 100 and as the reagent management information about the R3 reagent container 120. Further, the descent adjustment amount and the previous-descent amount about the R1 reagent, and the descent adjustment amount and the previous-descent amount about the R3 reagent, are stored in the reagent DB separately.

Subsequently, the CPU 201 calculates, for the R1 reagent, a difference between the descent adjustment amount of the current measurement mechanism unit 2 and the descent adjustment amount that was previously obtained (i.e., one read from the RFID tag 104 and stored in the reagent DB) (e.g., (Mb−Ma) in FIG. 10) (S16). Specifically, the CPU 201 reads, from the battery backup RAM 204, the descent adjustment amount of the current sample analyzer about the R1 reagent (e.g., Ma in FIG. 10). The CPU 201 also reads the descent adjustment amount about the R1 reagent that has been read from the RFID tag 104 of the R1/R3 reagent container and stored in the reagent DB (e.g., Mb in (b) of FIG. 10). Then, the CPU 201 calculates a difference between these descent adjustment amounts (e.g., (Mb−Ma) in FIG. 10). Similarly, for the R3 reagent, the CPU 201 calculates a difference between the descent adjustment amount of the current measurement mechanism unit 2 and the descent adjustment amount that was previously obtained (i.e., one read from the RFID tag 104 and stored in the reagent DB) (S16).

If the difference calculated at S16 is not 0 (i.e., there is a difference) (S17: YES), the processing proceeds to S18. If the difference calculated at S16 is 0 (i.e., there is no difference) (S17: NO), the processing proceeds to S21.

If there is a difference (S17: YES), the CPU 201 writes the descent adjustment amount of the current measurement mechanism unit 2 about the R1 reagent (e.g., Ma of FIG. 10) and the descent adjustment amount of the current measurement mechanism unit 2 about the R3 reagent into the RFID tag 104 as the descent adjustment amount about the R1 reagent and the descent adjustment amount about the R3 reagent (S18). Then, the CPU 201 writes the corresponding-descent amount about the R1 reagent and the corresponding-descent amount about the R3 reagent into the RFID tag 104 as the previous-descent amount about the R1 reagent and the previous-descent amount about the R3 reagent (S19). To be specific, a value resulting from adding the difference calculated at S16 for the R1 reagent to the previous-descent amount about the R1 reagent that has been read from the RFID tag 104 of the R1/R3 reagent container and stored in the reagent DB (i.e., the corresponding-descent amount), and a value resulting from adding the difference calculated at S16 for the R3 reagent to the previous-descent amount about the R3 reagent that has been read from the RFID tag 104 of the R1/R3 reagent container and stored in the reagent DB (i.e., the corresponding-descent amount), are written into the RFID tag 104. Further, the CPU 201 updates the previous-descent amount about the R1 reagent and the previous-descent amount about the R3 reagent that are stored in the reagent DB, with the corresponding-descent amount about the R1 reagent and the corresponding-descent amount about the R3 reagent (S20).

Next, the CPU 201 determines whether the process steps S13 to S20 have been completed for all the R1/R3 reagent containers (S21). If the process steps S13 to S20 have not been completed for all the R1/R3 reagent containers (S21: NO), the processing returns to S13. If the process steps S13 to S20 have been completed for all the R1/R3 reagent containers (S21: YES), the measurement preparation process ends.

Although the measurement preparation process has been described only for the R1/R3 reagent containers, the measurement preparation process is performed also for the R2 reagent containers in the same manner as described above.

Figure 14:
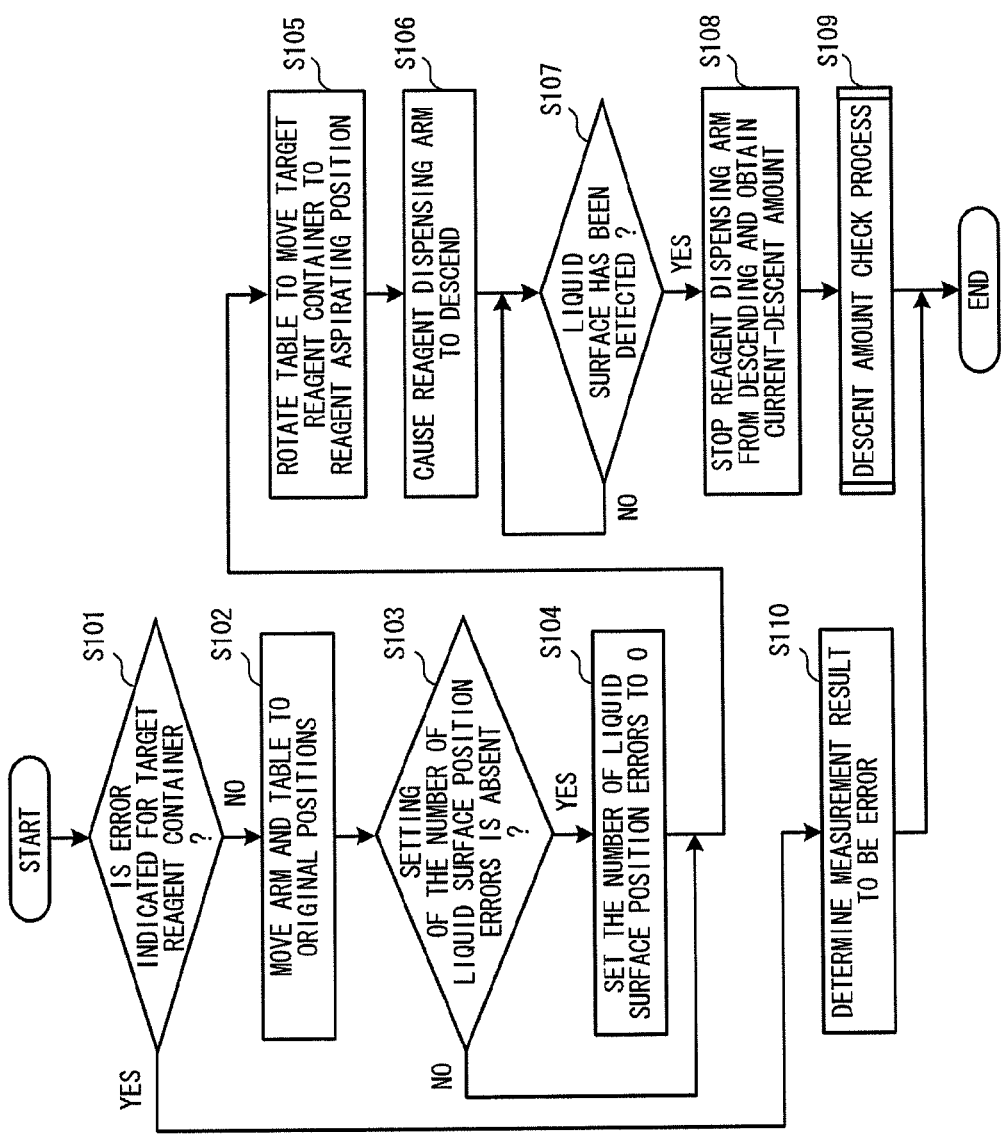
FIG. 14 is a flowchart showing a measurement process and a reagent aspirating process according to the embodiment.

Shown in (a) of FIG. 14 is a flowchart that shows a measurement process performed by the measurement mechanism unit 2. The measurement process starts when the measurement start button 522 as shown in FIG. 12 is pressed after order registration is performed. A job list is created based on the order registration (see FIG. 16). The measurement process is performed on each sample registered in the job list. A plurality of measurement items may be set for each sample (e.g., "HBsAg", "HCVAb", "PSA", etc., shown in FIG. 16). Each measurement item is associated in advance with reagent containers that are used in measurement of the measurement item. Multiple reagent containers containing reagents for use in measurement of the same measurement item are set on the inner table 162 and the outer table 163 as shown in FIG. 3. Among these reagent containers, a predetermined reagent container is set as a reagent container to be used in the measurement of the measurement item (i.e., a target reagent container). The other reagent containers are set as spare reagent containers that are used when an error has occurred in the target reagent container.

It should be noted that, in the measurement process, control of the inner table 162 in relation to R1/R3 reagent containers, control of the outer table 163 in relation to R2 reagent containers 110, and control of the R1 to R3 reagent dispensing arms, are performed in parallel.

When the measurement start button 522 is pressed, the CPU 201 of the measurement mechanism unit 2 performs measurement in accordance with the job list which is created based on the order registration (S31). In this measurement, each of the R1 to R3 reagent dispensing arms performs a reagent aspirating process. If the CPU 201 determines that the jobs in the job list have not been entirely completed (S32: NO), the CPU 201 continues the measurement at S31. When all the jobs are completed (S32: YES), the CPU 201 ends the measurement process.

Shown in (b) of FIG. 14 is a flowchart that shows the reagent aspirating process which is performed by each of the R1 to R3 reagent dispensing arms in the measurement performed at S31 in (a) of FIG. 14. It should be noted that the CPU 201 of the measurement mechanism unit 2 starts the reagent aspirating process in accordance with the job list, and the reagent aspirating process is performed by each of the R1 to R3 reagent dispensing arms in parallel. For the purpose of facilitating the understanding, only the reagent aspirating process which the R1 reagent dispensing arm 6 performs on an R1 reagent container held by the inner table 162 is described below. However, the R2 reagent dispensing arm performs the reagent aspirating process on an R2 reagent container and the R3 reagent dispensing arm performs the reagent aspirating process on an R3 reagent container in the same manner as described below.

First, the CPU 201 of the measurement mechanism unit 2 determines whether an error is indicated for an R1 reagent container 100 from which the R1 reagent is to be aspirated (hereinafter, this R1 reagent container 100 may be referred to as a "target R1 reagent container 100") (S101). If it is determined that an error is indicated for the target R1 reagent container 100 (S101: YES), the CPU 201 determines the result of the measurement to be an error (S110) and ends the reagent aspirating process. If it is determined that an error is not indicated for the target R1 reagent container 100 (S101: NO), the CPU 201 causes the R1 reagent dispensing arm 6 and the inner table 162 to move to their original positions (S102).

Next, the CPU 201 determines whether a setting of the number of liquid surface position errors is absent for the target R1 reagent container 100 (S103). The number of liquid surface position errors will be described below. If a setting of the number of liquid surface position errors is absent for the target R1 reagent container 100 (S103: YES), the number of liquid surface position errors is set to "0" for the target R1 reagent container 100 (S104). The number of liquid surface position errors is stored in the RAM 203 of the measurement mechanism unit 2.

Next, the CPU 201 causes the inner table 162 to rotate, thereby moving the target R1 reagent container 100 to a reagent aspirating position (S105), and drives the stepping motor 6b, thereby causing the pipette 6a of the R1 reagent dispensing arm 6 to descend (S106). The CPU 201 continues to cause the pipette 6a to descend until the liquid level sensor 6e detects the liquid surface of the R1 reagent (S107).

When the liquid surface of the R1 reagent is detected (S107: YES), the CPU 201 stops the pipette 6a from descending, and obtains the number of pulses outputted from the rotary encoder 6c, that is, obtains the length (represented as the number of pulses) from the original position of the pipette 6a to the liquid surface of the R1 reagent (hereinafter, referred to as a "current-descent amount") (S108). Next, the CPU 201 performs a "descent amount check process" (S109). Then, the reagent aspirating process performed on the target R1 reagent container 100 ends.

Figure 15:
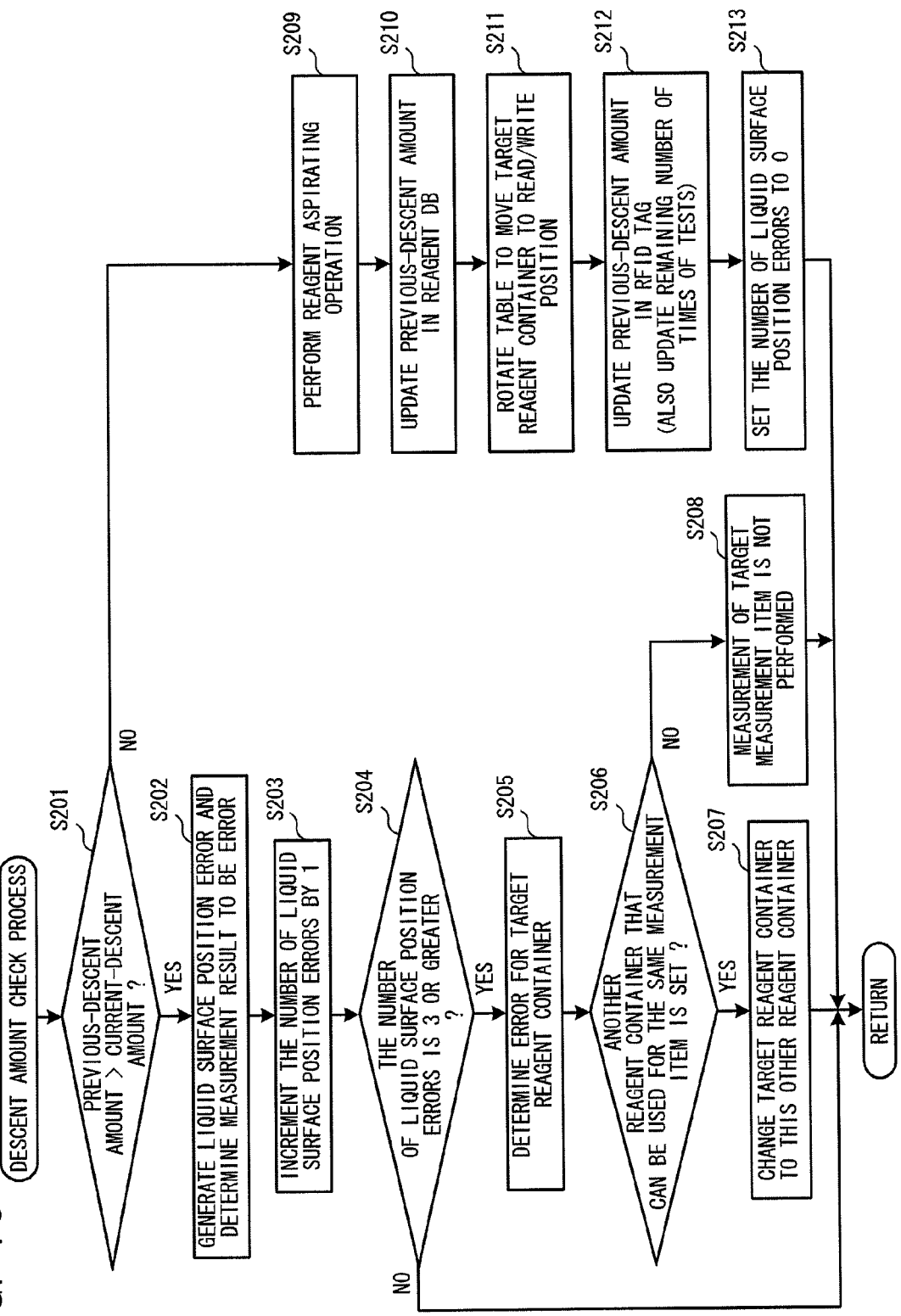
FIG. 15 is a flowchart showing a descent amount check process according to the embodiment.

FIG. 15 is a flowchart showing the "descent amount check process". Hereinafter, the "descent amount check process" will be described only in relation to the reagent aspirating process performed by the R1 reagent dispensing arm 6. It should be noted that if there is a difference between the descent adjustment amount of the previous measurement mechanism unit 2 and the descent adjustment amount of the current measurement mechanism unit 2, the previous-descent amount stored in the reagent DB of the current measurement mechanism unit 2 is updated, at S20 of FIG. 13, with a value that results from adding the difference to the previous-descent amount read from the RFID tag, that is, updated with the corresponding-descent amount described above with reference to (b) of FIG. 11. In this case, the corresponding-descent amount is used as the previous-descent amount in the "descent amount check process" of FIG. 15.

First, the CPU 201 of the measurement mechanism unit 2 compares the previous-descent amount about the R1 reagent stored in the reagent DB with the current-descent amount obtained at S108 of FIG. 14, and determines whether the previous-descent amount is greater than the current-descent amount (S201). If the previous-descent amount is greater than the current-descent amount (S201: YES), the process proceeds to S202. If the previous-descent amount is not greater than the current-descent amount (S201: NO), the processing proceeds to S209.

In the previous measurement mechanism unit 2, the timing for performing reagent aspiration is after obtaining the previous-descent amount. Therefore, generally speaking, the current-descent amount obtained at S108 of FIG. 14 is greater than the previous-descent amount about the R1 reagent that is stored in the reagent DB, by an amount corresponding to a reagent amount aspirated in the reagent aspiration by the previous measurement mechanism unit 2. However, if bubbles are being formed at the liquid surface of the R1 reagent in the R1 reagent container 100 in the current measurement mechanism unit 2, it is possible that the current-descent amount obtained at S108 of FIG. 14 is less than or equal to the previous-descent amount about the R1 reagent that is stored in the reagent DB. That is, in the determination of S201, it is determined "YES" when it is likely that bubbles are being formed at the liquid surface of the R1 reagent, and it is determined "NO" when it is unlikely that bubbles are being formed at the liquid surface of the R1 reagent.

When it is likely that bubbles are being formed at the liquid surface of the R1 reagent (S201: YES), the CPU 201 generates a liquid surface position error and determines the result of the measurement to be an error, and then transmits the measurement result error to the control apparatus 4 (S202). Accordingly, the measurement item of the current job is masked in the job list displayed on the display unit 420 of the control apparatus 4. Then, the CPU 201 increments the number of liquid surface position errors about the R1 reagent container 100 by 1 (S203).

In this case, the measurement of the measurement item of the current job ends. Thereafter, the R1 reagent as well as the other reagents (R2 and R3 reagents) are not aspirated for the measurement item of this job. However, as described below, the R1 reagent may be aspirated from the R1 reagent container 100 for a different measurement item other than the measurement item of this job (e.g., a measurement item of a different job, in which the R1 reagent is used).

Figure 16:
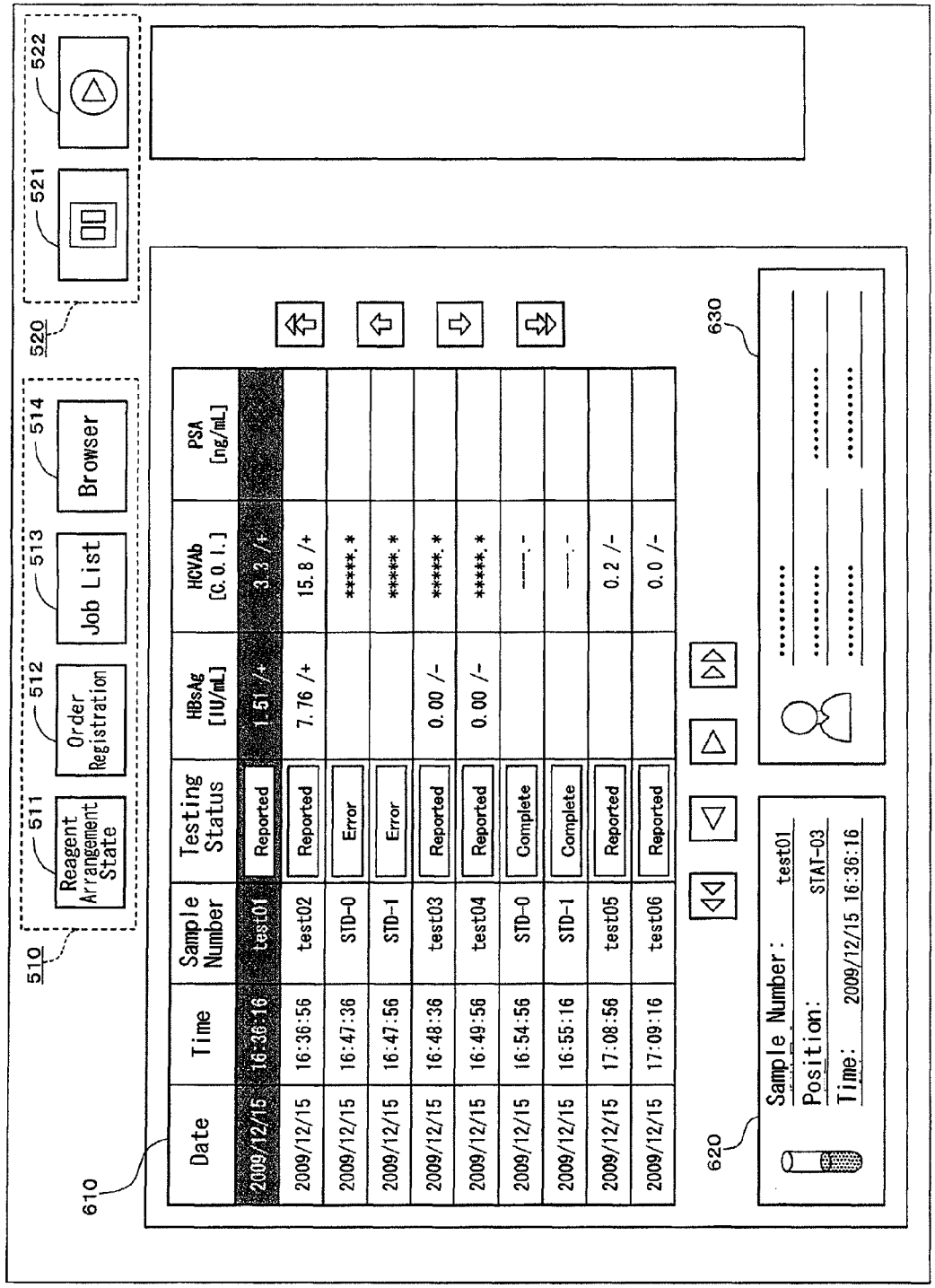
FIG. 16 shows an example of a job list screen displayed on the display unit of the control apparatus according to the embodiment.

FIG. 16 shows an example of a job list screen displayed on the display unit 420 of the control apparatus 4. The job list screen includes: the display screen selection area 510 and the measurement instruction area 520 which are the same as those shown in FIG. 12; a job list display area 610; a sample information display area 620; and a patient information display area 630.

The job list display area 610 shows jobs including multiple types of measurements that are performed on each sample. For example, two measurement items ("HBsAg" and "HCVAb") are set for a job that is shown in the first line in the job list (sample number "test 01"). When measurement results are received from the measurement mechanism unit 2 regarding the measurement items, the measurement results are displayed in corresponding cells in the job list. Scroll buttons for vertically scrolling the displayed contents are provided to the right of the job list display area 610, and scroll buttons for horizontally scrolling the displayed contents are provided below the job list display area 610.

The sample information display area 620 shows information about a sample measured in a job that has been selected by the user and thus highlighted in the job list display area 610 (e.g., the job shown in the first line in the job list). The patient information display area 630 shows information about a patient from whom the sample was collected.

Upon receiving the measurement result error from the measurement mechanism unit 2 at S202 of FIG. 15, the CPU 401 of the control apparatus 4 masks the measurement result of the measurement item in the display. Thus, for example, the measurement result is shown as "*****.*" in the same manner as shown in the third to sixth lines in the job list regarding the measurement item "HCVAb".

It should be noted that a measurement result is masked in the display (i.e., "******.*") not only when a liquid surface position error has occurred in the "descent amount check process" for any of the R1 to R3 reagents, but also when a different error has occurred. When an error has occurred, the user instructs to display an error details screen which includes an error list. Such an error list is generated for each measurement item. The error details screen allows the user to specify the cause of an error that has occurred for a measurement item for which the measurement result is masked in the display.

Figure 17:
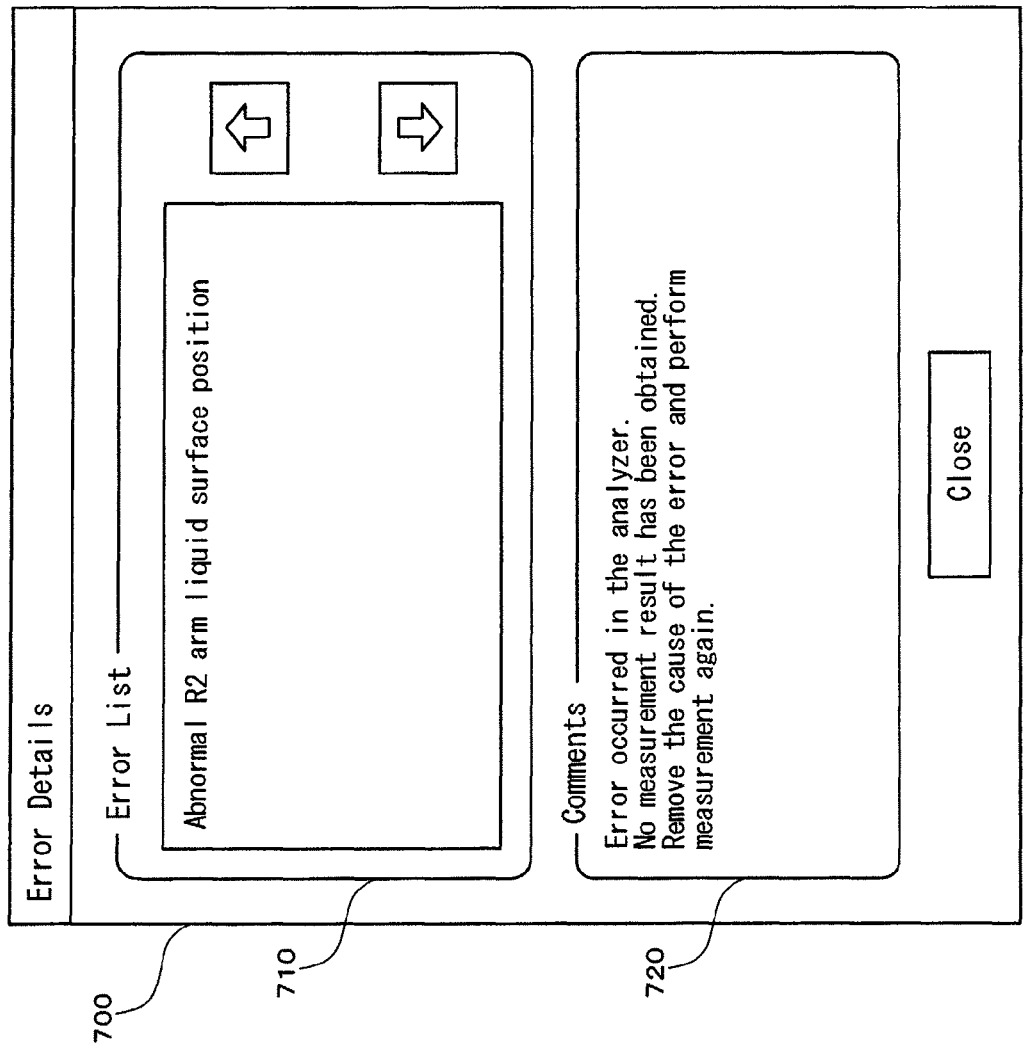
FIG. 17 shows an example of an error details screen displayed on the display unit of the control apparatus according to the embodiment.

FIG. 17 shows an example of an error details screen 700 which is displayed on the display unit 420 of the control apparatus 4. The error details screen 700 is displayed when one of error display buttons in a list screen (not shown) which shows details of measurement results is pressed, which list screen is displayed when the browser button 514 is pressed. The error display buttons are provided for respective measurement items for which errors have occurred.

In the error details screen 700, an error list display area 710 shows an error list which indicates errors that have occurred in one measurement item. In this example, errors that have occurred in one measurement item include "abnormal R2 arm liquid surface position". This indicates that, in the "descent amount check process" performed by the R2 reagent dispensing arm 7, a liquid surface position error has been generated at S202 regarding a target R2 reagent container 110. By viewing a comment display area 720 in the error details screen 700, the user can know, for example, the current status of the measurement process being performed and how to handle the liquid surface position error.

Referring to FIG. 15 again, next, if the CPU 201 of the measurement mechanism unit 2 determines that the number of liquid surface position errors is three or greater (S204: YES), then the CPU 201 determines an error for the R1 reagent container 100, and transmits the error to the control apparatus 4 (S205). Accordingly, in the display screen of FIG. 12 which is displayed on the display unit 420 of the control apparatus 4, a reagent indicium, shown in the reagent arrangement display area 540, that corresponds to the R1 reagent container 100 is displayed in a manner as shown in a holding position (12) in the inward area or a holding position (25) in the outward area.

Subsequently, the CPU 201 determines whether the inner table 162 is holding another R1 reagent container 100 that can be used for the same measurement item (S206). If the inner table 162 is holding another R1 reagent container 100 that can be used for the same measurement item (S206: YES), the CPU 201 changes the target R1 reagent container for the measurement item from the R1 reagent container 100 for which the error is indicated to this other R1 reagent container 100 (S207).

On the other hand, if the inner table 162 is not holding another R1 reagent container 100 that can be used for the same measurement item (S206: NO), the CPU 201 does not perform the measurement of the measurement item of the current job (S208). In this case, since the inner table 162 is holding no other R1 reagent container 100 from which the R1 reagent can be aspirated, the R1 reagent cannot be used in any jobs thereafter. Accordingly, if it is determined at S101 in (b) of FIG. 14 that an error is indicated for the target R1 reagent container 100 (S101: YES), then the result of the measurement is determined to be an error (S110). Accordingly, the reagent aspirating process ends.

If the CPU 201 determines that the number of liquid surface position errors is not greater than or equal to three (S204: NO), the "descent amount check process" ends. In this case, there is a possibility that the bubbles formed at the liquid surface of the R1 reagent disappear after a while. Therefore, an error is not indicated for the R1 reagent container 100 so that the R1 reagent may be aspirated from the R1 reagent container 100 for the same measurement item in a different job.

Next, if it is determined at S201 that the previous-descent amount is not greater than the current-descent amount (S201: NO), then it is unlikely that bubbles are being formed at the liquid surface of the R1 reagent in the R1 reagent container 100. Accordingly, the CPU 201 performs a reagent aspirating operation (S209). That is, the pipette 6a contacting the liquid surface is further moved in the downward vertical direction by an amount that corresponds to an amount to be aspirated of the R1 reagent. Then the R1 reagent is aspirated by the amount.

Subsequently, the CPU 201 updates, with the current-descent amount obtained at S108 of FIG. 14, the previous-descent amount that is stored in the reagent DB in association with the R1 reagent container 100 (S210). Further, the CPU 201 causes the inner table 162 to rotate, thereby locating the R1 reagent container 100 at the read/write position 162f (S211). Then, the CPU 201 updates, with the current-descent amount obtained at S108 of FIG. 14, the previous-descent amount about the R1 reagent that is written in the RFID tag 104 (S212). Still further, the CPU 201 reduces the remaining reagent amount, stored in the reagent DB, of the R1 reagent container 100 in accordance with the amount of the R1 reagent that has been aspirated at this time. Still further, the CPU 201 updates the remaining reagent amount written in the RFID tag 104 with the remaining reagent amount, stored in the reagent DB, of the R1 reagent container 100 (S212). Still further, the CPU 201 sets the number of liquid surface position errors to zero (S213). Then, the "descent amount check process" ends.

As described above, according to the present embodiment, in a reagent aspirating operation, when a reagent has been aspirated from a reagent container, the descent amount of the pipette that is obtained at the time of detecting the liquid surface (the current-descent amount) of the reagent is written into the item of previous-descent amount in the RFID tag affixed to the reagent container. Therefore, even if this reagent container is later set in the measurement mechanism unit 2 of another sample analyzer, the descent amount of the pipette in the reagent aspirating operation previously performed on the reagent container can be obtained by reading the previous-descent amount written in the RFID tag affixed to the reagent container.

Further, according to the present embodiment, the descent amount of the pipette at the time of aspirating a reagent in the previous measurement mechanism unit 2 (the previous-descent amount), and the descent adjustment amount of the previous measurement mechanism unit 2, are written in the RFID tag. Therefore, based on the previous-descent amount and the descent adjustment amount read from the RFID tag as well as the descent adjustment amount of the current measurement mechanism unit 2, the descent amount for the pipette in the current measurement mechanism unit 2 (the corresponding-descent amount) can be obtained. Accordingly, even if the height of the pipette and the height of the reagent container bottom face are different between the previous measurement mechanism unit 2 and the current measurement mechanism unit 2 due to assembly errors or the like of these measurement mechanism units 2 (i.e., even if a reagent container previously used in the sample analyzer 1 is set in another sample analyzer 1 and sample measurement is performed by using the reagent of the reagent container), whether the liquid surface position of the reagent has been properly detected in the current measurement mechanism unit 2 can be accurately determined by comparing the corresponding-descent amount with the current-descent amount.

Still further, according to the present embodiment, the descent adjustment amount can be obtained in a simple manner described above with reference to FIG. 10, i.e., set the container body 101 having the jig 130 attached thereto on the inner table 162.

Still further, according to the present embodiment, if the previous-descent amount is greater than the current-descent amount, the measurement result is determined to be an error, and reagent aspiration is not performed. Thus, for example, measurement is prevented from being performed in a situation where a proper amount of reagent cannot be aspirated since bubbles are being formed at the liquid surface of the reagent. Accordingly, erroneous sample measurement can be assuredly prevented.

Still further, according to the present embodiment, if the previous-descent amount is greater than the current-descent amount, the measurement is determined to be an error before reagent aspiration is performed (S201 and S202 in FIG. 15). Thus, unnecessary reagent aspiration can be prevented.

Still further, according to the present embodiment, the error details screen 700 as shown in FIG. 17 is displayed. Therefore, by viewing the error details screen 700, the user can easily know that an error has occurred in relation to the liquid surface of a reagent in a reagent container. By viewing the screen, the user can also know, for example, the status of measurement being performed in the current job.

Still further, according to the present embodiment, the screen as shown in FIG. 12 is displayed. By viewing the screen, the user can easily know whether an error is being indicated for any reagent container. This allows the user to perform replacement of a reagent container as necessary.

The embodiment of the present invention has been described as above. However, the present invention is not limited to the above embodiment.

For example, although blood is measured in the above embodiment, urine may also or alternatively be measured. Thus, for example, the present invention is applicable to sample analyzers for testing urine samples. Further, the present invention is applicable to laboratory sample testing apparatuses for testing other types of clinical samples.

In the above embodiment, as shown in FIG. 10, a container body having a jig fitted in its top opening is used to measure the descent adjustment amount for each of the R1 to R3 reagents. However, the preset invention is not limited thereto. The descent adjustment amount may be measured by using a jig that is set at the cuvette setting part 9a.

Figure 18:
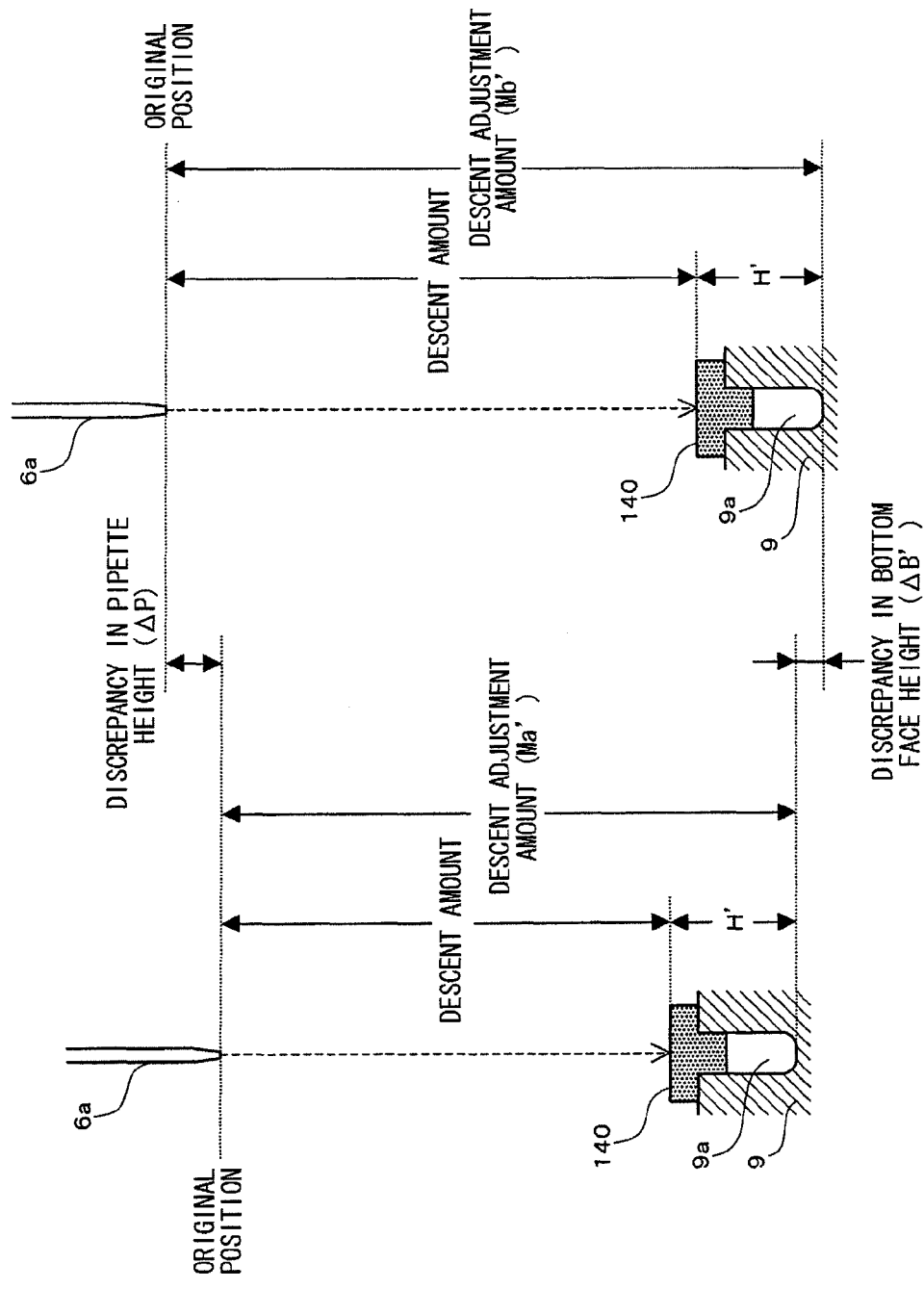
FIG. 18 illustrates a variation of a process of obtaining the descent adjustment amount according to the embodiment.

FIG. 18 illustrates a variation of the manner of obtaining the descent adjustment amount, in which a jig 140 set at the cuvette setting part 9a is used.

In this case, the descent adjustment amount of the previous measurement mechanism unit 2 about the R1 reagent is Ma' as shown in (a) of FIG. 18, and the descent adjustment amount of the current measurement mechanism unit 2 about the R1 reagent is Mb' as shown in (b) of FIG. 18. A difference between these descent adjustment amounts (Mb'−Ma') is calculated by an equation shown below if discrepancies between the previous measurement mechanism unit 2 and the current measurement mechanism unit 2 are as follows: a discrepancy in the height of the pipette 6a is ΔP; and a discrepancy in the height of the bottom face of the cuvette setting part 9a is ΔB'.

$$Mb'-Ma'=\Delta P+\Delta B' \quad (4)$$

It can be considered that the discrepancy ΔB' in the height of the bottom face of the cuvette setting part 9a is substantially equal to the discrepancy ΔB in the height of the bottom face of the container body shown in FIG. 10. Accordingly, based on the above equations (2) and (4), the corresponding-descent amount (Zb) is represented by an equation below.

$$Zb=Za+(Mb'-Ma') \quad (5)$$

As shown in the above equation (5), the corresponding-descent amount (Zb) shown in (b) of FIG. 11 can be obtained by adding the difference (Mb'−Ma') between the descent adjustment amounts to the previous-descent amount (Za). It should be noted that, also in each of the cases of an R2 reagent container 110 and an R3 reagent container 120, the corresponding-descent amount can be obtained in a similar manner. That is, in the case of an R2 reagent container 110 (or R3 reagent container 120), the corresponding-descent amount can be obtained by adding the difference between the descent adjustment amounts about the R2 reagent (or R3 reagent) to the previous-descent amount about the R2 reagent (or R3 reagent).

In the above embodiment, the descent adjustment amount of each analyzer is stored in the battery backup RAM 204 of the measurement mechanism unit 2. However, the present invention is not limited thereto. As an alternative, the descent adjustment amount may be stored in a battery backup RAM provided in the control apparatus 4, or the hard disk 404 of the control apparatus 4, or a host computer that is connected via a communication network to the measurement mechanism unit 2.

Further, in the above embodiment, the reagent management information is stored in a non-contact type IC tag (RFID tag), and the reagent management information is written into, or read from, the non-contact type IC tag (RFID tag) by means of wireless communication using radio waves. However, the present invention is not limited thereto. The reagent management information may be stored in a contact type IC tag, and the reagent management information may be written into, or read from, the contact type IC tag by means of wired communication using an IC tag reader/writer.

(Second Embodiment)

Hereinafter, a second embodiment of the present invention will be described. In the second embodiment, the configuration of the sample analyzer 1 is the same as that described above in the first embodiment. Therefore, the description of the configuration of the sample analyzer 1 is omitted in the second embodiment.

Figure 19:
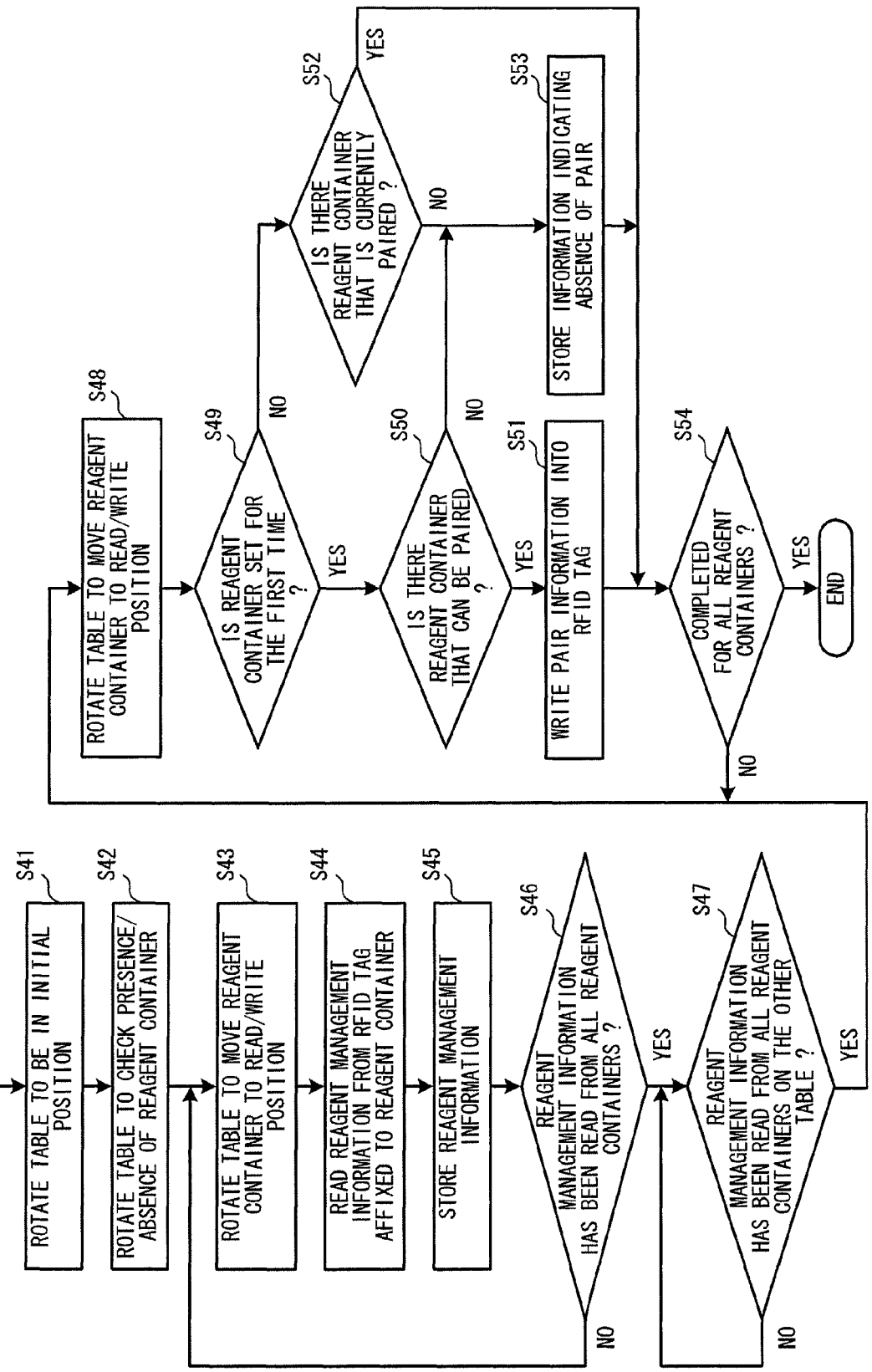
FIG. 19 is a flowchart showing a measurement preparation operation performed by each of an inner table and an outer table, according to another embodiment of the present invention.

FIG. 19 is a flowchart showing a measurement preparation operation performed by each of the inner table 162 and the outer table 163. The measurement preparation operation by the inner table 162 and the measurement preparation operation by the outer table 163 are performed in parallel when the measurement start button 522 as shown in FIG. 12 is pressed. Hereinafter, only the measurement preparation operation performed by the inner table 162 is described. It should be noted that, however, the measurement preparation operation is also performed by the outer table 163 in the same manner.

When the measurement start button 522 is pressed, the CPU 201 of the measurement mechanism unit 2 receives from the control apparatus 4 an instruction to perform the measurement preparation operation. Upon receiving the instruction, the CPU 201 drives the first stepping motor 162a to rotate the inner table 162 to be in an initial position (S41). In this manner, the rotational position of the inner table 162 is adjusted to be at the original position. Accordingly, rotational positions of the inner table 162 thereafter are located at proper positions. Next, the CPU 201 causes the inner table 162 to rotate, thereby checking whether each of the holders of the inner table 162 is holding an R1/R3 reagent container (S42). In this checking operation, the light emitter 164a and the light receiver 164b are used as described above.

Then, the CPU 201 causes the inner table 162 to rotate, thereby moving an R1/R3 reagent container to the read/write position 162f (S43). Subsequently, the CPU 201 reads reagent management information from the RFID tag 104 affixed to the R1 reagent container 100 by means of the antenna 162b (S44), and stores the read reagent management information in the RAM 203 of the measurement mechanism unit 2 in association with the holders holding the R1/R3 reagent container (S45).

Next, the CPU 201 determines whether reagent management information has been read from all the R1/R3 reagent containers on the inner table 162 (S46). If reagent management information has been read from all the R1/R3 reagent containers on the inner table 162 (S46: YES), the processing proceeds to S47. On the other hand, if the reading of reagent management information from all the R1/R3 reagent containers on the inner table 162 has not yet been completed (S46: NO), the processing returns to S43 at which the same process is performed on an R1/R3 reagent container held by the next holder.

At the next step, the CPU 201 does not advance the processing until reagent management information is read from all the R2 reagent containers 110 on the outer table 163 (S47). If reagent management information has been read from all the R2 reagent containers 110 on the outer table 163, this means that the reagent management information about all the R2 reagent containers 110 on the outer table 163 has been stored in the RAM 203 of the measurement mechanism unit 2.

Then, the CPU 201 causes the inner table 162 to rotate, thereby moving an R1/R3 reagent container to the read/write position 162f (S48). The CPU 201 determines whether the R1/R3 reagent container located at the read/write position 162f is set on the inner table 162 for the first time (S49). To be specific, the CPU 201 determines based on the reagent management information stored in the RAM 203 whether identification information is present in the item of pair information about the R1/R3 reagent container. If identification information is not present in the item of pair information, it is determined that the R1/R3 reagent container is set on the inner table 162 for the first time. On the other hand, if identification information is present in the item of pair information, it is determined that the R1/R3 reagent container is not set on the inner table 162 for the first time.

If it is determined that the R1/R3 reagent container is set on the inner table 162 for the first time (S49: YES), the CPU 201 determines whether the outer table 163 is holding an R2 reagent container 110 that can be paired with the R1/R3 reagent container (S50). To be specific, the CPU 201 determines based on the reagent management information stored in the RAM 203 whether the outer table 163 is holding an R2 reagent container 110 that is set on the outer table 163 for the first time (i.e., there is no identification information as pair information about the R2 reagent container 110) and whose measurement item is the same as that of the R1/R3 reagent container.

If the outer table 163 is holding an R2 reagent container 110 that can be paired with the R1/R3 reagent container (S50: YES), the CPU 201 writes, into the item of pair information about the R1/R3 reagent container, the identification information about the R2 reagent container 110 that is to be paired with the R1/R3 reagent container (S51). On the other hand, if the outer table 163 is holding no R2 reagent container 110 that can be paired with the R1/R3 reagent container (S50: NO), the CPU 201 stores, in the RAM 203, information indicating the absence of a pair regarding the R1/R3 reagent container (S53).

On the other hand, if it is determined that the R1/R3 reagent container is not set on the inner table 162 for the first time (S49: NO), the CPU 201 determines whether the outer table 163 is holding an R2 reagent container 110 currently paired with the R1/R3 reagent container (S52). To be specific, the CPU 201 determines based on the reagent management information stored in the RAM 203 whether the outer table 163 is holding an R2 reagent container 110 whose identification information is the same as the identification information written in the item of pair information about the R1/R3 reagent container.

If the outer table 163 is holding an R2 reagent container 110 currently paired with the R1/R3 reagent container (S52: YES), the processing proceeds to S54. On the other hand, if the outer table 163 is holding no R2 reagent container 110 currently paired with the R1/R3 reagent container (S52: NO), the CPU 201 stores, in the RAM 203, information indicating the absence of a pair regarding the R1/R3 reagent container (S53).

Next, at S54, the CPU 201 determines whether the process steps S48 to S53 have been completed for all the R1/R3 reagent containers held by the inner table 162. The CPU 201 repeats the process steps S48 to S53 until the process steps S48 to S53 have been completed for all the R1/R3 reagent containers held by the inner table 162. When the process steps S48 to S53 have been completed for all the R1/R3 reagent containers held by the inner table 162 (S54: YES), the measurement preparation operation by the inner table 162 ends.

It should be noted that, when the measurement preparation operation by the inner table 162 ends, the CPU 201 transmits, to the control apparatus 4 via the communication interface 205, the reagent management information stored in the RAM 203 as well as the information that is stored in the RAM 203 when the process at S53 is performed. Based on the received information, the CPU 401 of the control apparatus 4 displays, on the display unit 420, a screen that shows an arrangement state of reagents as shown in FIG. 12. Here, the reagent indicium of a reagent container for which the process at S53 has been performed is enclosed by a heavy line as described above. Further, if a reagent container is set on the inner table 162 (or outer table 163) for the first time, the remaining reagent amount indicated in the content indicating portion 541 (or 542) of the reagent indicium of the reagent container is the filling amount contained in the reagent management information about the reagent container. On the other hand, if a reagent container is not set on the inner table 162 (or outer table 163) for the first time, the remaining reagent amount indicated in the content indicating portion 541 (or 542) of the reagent indicium of the reagent container is the remaining reagent amount contained in the reagent management information about the reagent container.

As described above, according to the present embodiment, when an R1/R3 reagent container is set on the inner table 162 for the first time, if the outer table 163 is holding an R2 reagent container 110 that can be paired with the R1/R3 reagent container, the identification information stored in the RFID tag 114 of the R2 reagent container 110 is written into the item of pair information in the RFID tag 104 of the R1/R3 reagent container. Similarly, when an R2 reagent container 110 is set on the outer table 163 for the first time, if the inner table 162 is holding an R1/R3 reagent container that can be paired with the R2 reagent container 110, the identification information stored in the RFID tag 104 of the R1/R3 reagent container is written into the item of pair information in the RFID tag 114 of the R2 reagent container 110. In this manner, in the RFID tag of each of these reagent containers, the identification information about a reagent container paired therewith is written. Therefore, even if these R1/R3 reagent containers and R2 reagent containers 110 are set in another sample analyzer, this other sample analyzer can accurately determine, for each of the reagent containers, a reagent container paired therewith.

As described above, from the RFID tag of each reagent container, information that specifies a reagent container paired therewith is obtained, and the reagent container paired therewith is determined based on the information. This prevents a wrong pair of reagents from being used in measurement of a predetermined measurement item. For example, if the reagent of one of reagent containers that are paired with each other is misused, then even if the reagents of these reagent containers are properly used in combination with each other thereafter, the reagent having been misused is used up before the reagent of the other reagent container in the pair. Consequently, the other reagent, which is still remaining, has to be discarded. However, as described above, the present embodiment prevents a wrong pair of reagents from being used in measurement. This eliminates a situation where the reagent of one of reagent containers that are paired with each other is used up before the reagent of the other reagent container in the pair. As a result, a waste of resources, that is, a remaining reagent being discarded wastefully, can be prevented.

The second embodiment of the present invention has been described as above. However, the present invention is not limited to the above embodiments.

For example, although blood is measured in the second embodiment, urine may also or alternatively be measured. Thus, for example, the present invention is applicable to sample analyzers for testing urine samples. Further, the present invention is applicable to laboratory sample testing apparatuses for testing other types of clinical samples.

In the second embodiment, at S50, the CPU 201 determines whether the outer table 163 is holding an R2 reagent container 110 that is set on the outer table 163 for the first time (i.e., there is no identification information as pair information about the R2 reagent container 110) and whose measurement item is the same as that of the R1/R3 reagent container. However, the present invention is not limited thereto. At S50, the CPU 201 may determine whether the outer table 163 is holding an R2 reagent container 110 that is set on the outer table 163 for the first time (i.e., there is no identification information as pair information about the R2 reagent container 110) and whose measurement item and lot number are the same as those of the R1/R3 reagent container.

Further, in the second embodiment, the reagent management information is stored in a non-contact type IC tag (RFID tag), and the reagent management information is written into, or read from, the non-contact type IC tag (RFID tag) by means of wireless communication using radio waves. However, the present invention is not limited thereto. The reagent management information may be stored in a contact type IC tag, and the reagent management information may be written into, or read from, the contact type IC tag by means of wired communication using an IC tag reader/writer.

Figure 20:
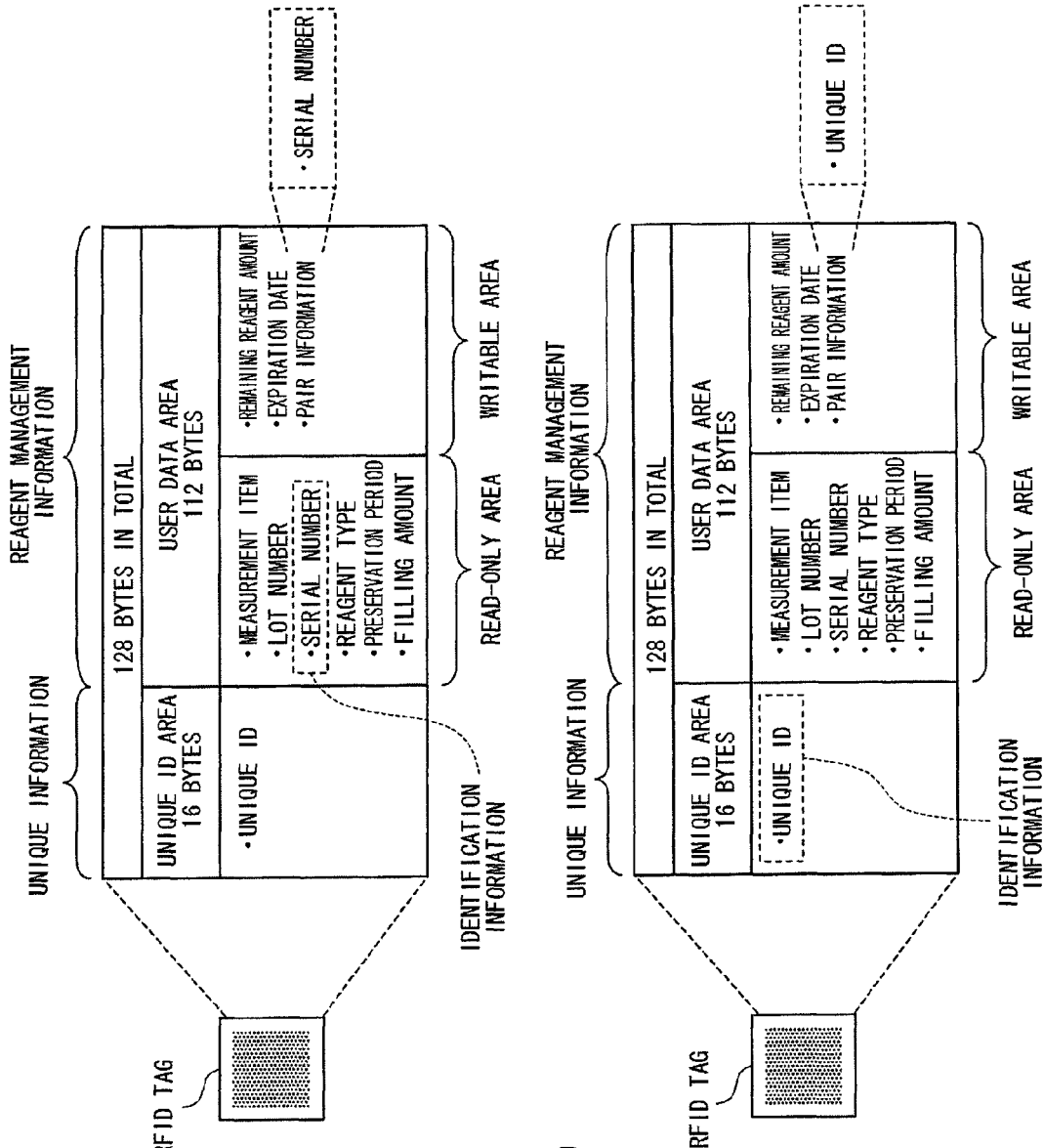
FIG. 20 is a conceptual diagram showing a variation of the unique information and the reagent management information which are stored in an RFID tag according to the embodiments.

FIG. 20 is a conceptual diagram showing a variation of the unique information and the reagent management information which are stored in an RFID tag according to the above embodiments. In the above embodiments, information written in the item of pair information about a reagent container includes the measurement item, lot number, and serial number of a reagent container paired therewith. However, the present invention is not limited thereto. As shown in (a) of FIG. 20, the information written in the item of pair information about a reagent container may only include the serial number of a reagent container paired therewith. As described above, the serial number of each reagent container allows the reagent container to be uniquely identified among other reagent containers for which the same measurement item and the same lot number are set. Reagent containers paired with each other share the same measurement item and the same lot number. Therefore, if a serial number is written as the identification information in the item of pair information about one reagent container, then similar to the above embodiments it is possible to uniquely identify a reagent container that is paired with said one reagent container, by referring to the measurement item and the lot number obtained from the read-only area of the RFID tag of said one reagent container as well as the serial number written in the item of pair information in the writable area of the RFID tag of said one reagent container.

Alternatively, as shown in (b) of FIG. 20, the information written in the item of pair information about one reagent container may include the unique ID that is stored in the unique ID area of the RFID tag of a reagent container that is paired with said one reagent container. As described above, the unique ID of each RFID tag allows the RFID tag to be uniquely identified among other RFID tags. Therefore, if a unique ID is written as the identification information in the item of pair information about one reagent container, then similar to the above embodiments it is possible to uniquely identify a reagent container that is paired with said one reagent container.

The pair information may be stored in the writable area in such a manner as to be protected from being overwritten. This prevents a situation where the pair information written in the RFID tag is overwritten with new pair information and thereby a new pair is created.

It should be noted that the embodiments described above are merely examples for implementing the present invention. The present invention is not limited by the above embodiments in any way.

What is claimed is:

1. A sample analyzer which performs analysis regarding a predetermined measurement item by using a combination of at least a first reagent and a second reagent, the sample analyzer comprising:
   a reagent container holder comprising an inner table configured to hold a first reagent container which contains the first reagent and which includes a first storage medium, and an outer table configured to hold a second reagent container which contains the second reagent and which includes a second storage medium;
   a communicator configured to:
      read information from the first storage medium and the second storage medium; and
      write information into the first storage medium and the second storage medium; and
   a controller configured to:
      determine a pairing of the first reagent container and the second reagent container;
      control the reagent container to rotate the inner table to move the first reagent container to an inner read/write position and to rotate the outer table to move the second reagent container to an outer read/write position; and
      control the communicator to read second identification information for identifying the second reagent container from the second storage medium and to write, into the first storage medium, the second identification information.

2. The sample analyzer of claim 1, wherein
   the first storage medium stores first reagent management information for managing the first reagent,
   the second storage medium stores second reagent management information for managing the second reagent.

3. The sample analyzer of claim 2, wherein
   each of the first reagent management information and the second reagent management information contains, at least, measurement item information and a lot number, and
   the controller is further configured to determine the pairing by determining the measurement item information that is obtained from the first storage medium and the measurement item information that is obtained from the second storage medium are the same.

4. The sample analyzer of claim 3, wherein
   the first reagent management information contains a first serial number that is assigned to the first reagent and the second reagent management information contains a second serial number that is assigned to the second reagent, and
   the controller is further configured to control the communicator to read the second serial number from the second storage medium and to write the second serial number into the first storage medium.

5. The sample analyzer of claim 4, wherein the controller is further configured to:
   control the communicator to read first identification information from the first storage medium; and
   determine based on the first identification information and the second identification information, whether the first reagent container is paired with the second reagent container.

6. The sample analyzer of claim 1, wherein
the first storage medium stores first unique information which is uniquely assigned to the first storage medium,
the second storage medium stores second unique information which is uniquely assigned to the second storage medium, and
the controller is further configured to control the communicator to obtain the second unique information from the second storage medium, and to control the communicator to write the obtained second unique information into the first storage medium.

7. The sample analyzer of claim 6, wherein the controller is further configured to, if the first unique identification information coincides with the second unique information determine that the first reagent container is paired with the second reagent container.

8. The sample analyzer of claim 1, wherein the communicator comprises:
a first antenna for reading information from the first storage medium and writing information into the first storage medium; and
a second antenna for reading information from the second storage medium and writing information into the second storage medium.

9. The sample analyzer of claim 1, wherein the first storage medium is a first RFID tag and the second storage medium is a second RFID tag.

10. The sample analyzer of claim 1, wherein the controller is further configured to control the communicator to write the second identification information into the first storage medium such that the second identification information is protected from being overwritten.

11. A reagent management method which combines a first reagent container containing a first reagent with a second reagent container containing a second reagent, the reagent management method comprising:
rotating an inner table to move the first reagent container to an inner read/write position;
rotating an outer table to move the second reagent container to an outer read/write position;
reading second identification information from a second storage medium which is a readable/writable storage medium and which is included in the second reagent container; and
writing the second identification information into a first storage medium which is a readable/writable storage medium and which is included in the first reagent container.

\* \* \* \* \*